United States Patent
Migawa et al.

(10) Patent No.: US 10,751,419 B2
(45) Date of Patent: *Aug. 25, 2020

(54) METHOD FOR SYNTHESIS OF REACTIVE CONJUGATE CLUSTERS

(71) Applicant: Ionis Pharmaceuticals, Inc., Carlsbad, CA (US)

(72) Inventors: Michael T. Migawa, Carlsbad, CA (US); Jinghua Yu, San Marcos, CA (US); W. Brad Wan, Fallbrook, CA (US); Sayten P. Patel, Mundelein, IL (US); Guillermo Vasquez, Oceanside, CA (US); Garth A. Kinberger, San Diego, CA (US); Thazha P. Prakash, Carlsbad, CA (US); Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,197

(22) Filed: Sep. 7, 2018

(65) Prior Publication Data

US 2019/0209694 A1 Jul. 11, 2019

Related U.S. Application Data

(63) Continuation of application No. 15/307,319, filed as application No. PCT/US2015/028732 on May 1, 2015, now Pat. No. 10,098,959.

(60) Provisional application No. 62/062,383, filed on Oct. 10, 2014, provisional application No. 61/986,966, filed on May 1, 2014.

(51) Int. Cl.
| | | |
|---|---|---|
| *C07H 1/00* | (2006.01) |
| *C07H 3/00* | (2006.01) |
| *C08B 37/00* | (2006.01) |
| *A61K 47/54* | (2017.01) |
| *C07H 15/04* | (2006.01) |
| *C07H 15/18* | (2006.01) |
| *C07H 21/00* | (2006.01) |

(52) U.S. Cl.
CPC ........... *A61K 47/549* (2017.08); *C07H 15/04* (2013.01); *C07H 15/18* (2013.01); *C07H 21/00* (2013.01)

(58) Field of Classification Search
None
See application file for complete search history.

(56) References Cited

PUBLICATIONS

Kikkeri et al. Chem. Commun. (2010), vol. 46, pp. 2197-2199.*

* cited by examiner

*Primary Examiner* — Patrick T Lewis
(74) *Attorney, Agent, or Firm* — McNeill Baur PLLC

(57) ABSTRACT

Provided herein are improved methods for the synthesis of reactive conjugate clusters and intermediates used in such methods. In particular, improvements are provided that enhance the synthesis of reactive conjugate clusters by reducing the number of synthetic steps required. The reactive conjugate clusters prepared using the improved methods don't include any transacylation impurities that are formed using existing methods. The improved methods also provide an increase in overall yield and a cost benefit over existing methods.

20 Claims, No Drawings

METHOD FOR SYNTHESIS OF REACTIVE CONJUGATE CLUSTERS

FIELD OF THE INVENTION

The present disclosure relates to the synthesis of reactive conjugate clusters and intermediates used in such methods. In particular, the present methods provide reactive conjugate clusters in fewer steps with higher purity compared to previously reported methods. The improved methods also provide an increase in overall yield and a cost benefit over existing methods.

BACKGROUND OF THE INVENTION

The synthesis of reactive conjugate clusters has been reported in numerous publications (see for example Maier et al., "Synthesis of Antisense Oligonucleotides Conjugated to a Multivalent Carbohydrate Cluster for Cellular Targeting," *Bioconjugate Chemistry*, 2003, (14): 18-29; Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808; and U.S. Pat. No. 8,507,661).

SUMMARY OF THE INVENTION

In certain embodiments, methods are provided for the synthesis of a reactive conjugate clusters having the formula:

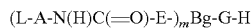

(L-A-N(H)C(=O)-E-)$_m$Bg-G-H wherein:
L is a ligand;
A is $C_2$ to $C_{10}$ alkyl optionally interrupted with one or more groups selected from —O—, —N(H)— and C(=O);
E is a single bond or $C_1$ to $C_{10}$ alkyl optionally interrupted with one or more groups selected from —O—, —N(H)— and C(=O);
Bg is a branching group;
G is a single bond or $C_1$ to $C_{10}$ alkyl optionally including one or more groups selected from —O—, —N(H)— and C(=O);
m is from 2 to about 6;
comprising:
reacting a pentafluorophenyl ester protected branching group having the formula:

(PFP—O—C(=O)-E-)$_m$Bg-G-Pg$_1$ wherein Pg$_1$ is a protecting group;
with at least m equivalents of a functionalized ligand having the formula:

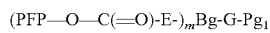

L-A-N(H)Pg$_2$ wherein Pg$_2$ is an amino protecting group;
in an organic solvent with a palladium catalyst and H$_2$ for a time and under conditions sufficient to provide the reactive conjugate cluster.

In certain embodiments, each E is $C_1$ to $C_4$ alkyl. In certain embodiments, each E is a single bond.

In certain embodiments, G is $C_1$ to $C_{10}$ alkyl optionally including one or more groups selected from —O—, —N(H)— and C(=O). In certain embodiments, G is —C(=O)—(CH$_2$)$_3$—C(=O)—O—. In certain embodiments, G is single bond between the branching group and H.

In certain embodiments, Pg$_1$ is a carboxyl protecting group. In certain embodiments, Pg$_1$ is a benzyl.

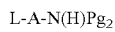

In certain embodiments, the branching group has the formula:

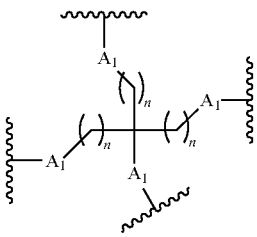

wherein:
each A$_1$ is, independently, CH$_2$, O or N(H); and
each n is, independently, 1 or 2.

In certain embodiments, the branching group has the formula:

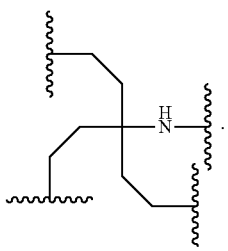 [SMILES: *CCC(CC*)(CC*)N*]

In certain embodiments, the branching group has the formula:

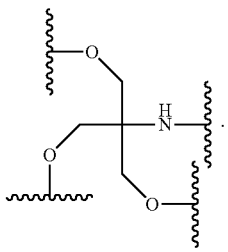 [SMILES: *NC(CO*)(CO*)CO*]

In certain embodiments, m is 3.

In certain embodiments, the pentafluorophenyl ester protected branching group has the formula:

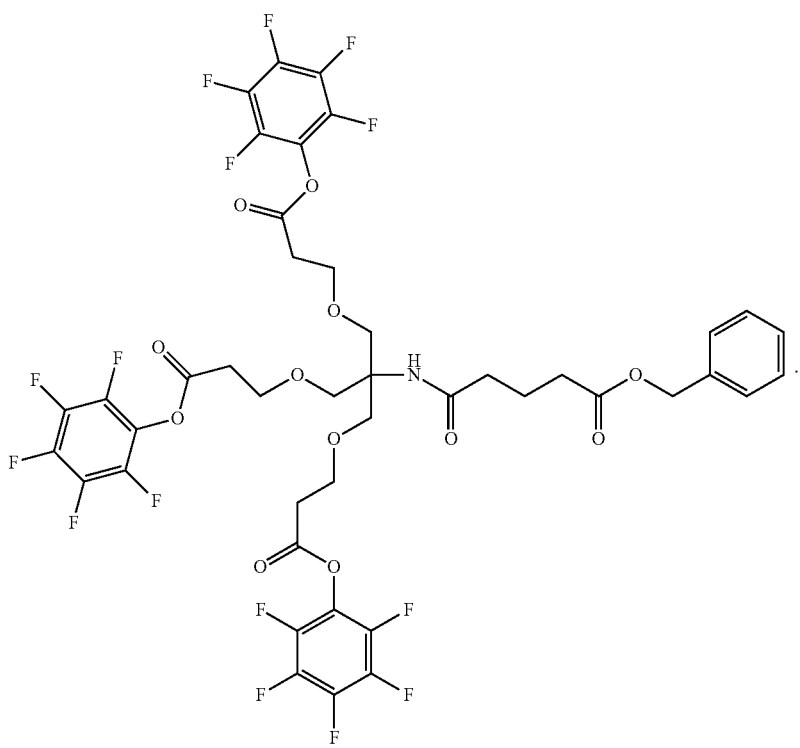 [SMILES: O=C(CCCC(=O)OCc1ccccc1)NC(COCCC(=O)Oc1c(F)c(F)c(F)c(F)c1F)(COCCC(=O)Oc1c(F)c(F)c(F)c(F)c1F)COCCC(=O)Oc1c(F)c(F)c(F)c(F)c1F]

In certain embodiments, the pentafluorophenyl ester protected branching group is at least about 95% pure.

In certain embodiments, each L has the formula:

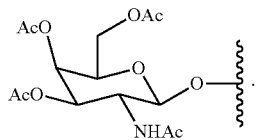

In certain embodiments, the functionalized ligand has the formula:

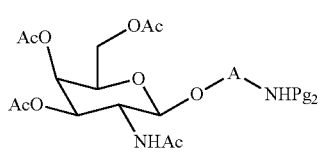

wherein

A is $C_2$ to $C_{10}$ alkyl optionally interrupted with one or more groups selected from —O—, —N(H)— and C(=O);

Pg$_2$ is an amino protecting group.

In certain embodiments, the functionalized ligand is prepared by treating a first intermediate having the formula:

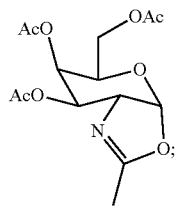 [SMILES: CC(=O)OCC1OC2OC(C)=NC2C(OC(C)=O)C1OC(C)=O]

with a second intermediate having the formula:

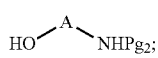

for a time and under conditions to provide the functionalized ligand; and wherein the first intermediate is prepared in situ by treatment of the protected galactose sugar having the formula:

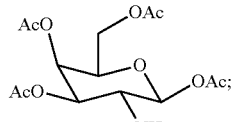

in an organic solvent with trimethylsilyl triflate (TMSOTf).

In certain embodiments, each A is $C_4$ to $C_8$ alkyl. In certain embodiments, each A is $C_4$ to $C_8$ alkyl interrupted with one amide group (—N(H)—C(=O)—).

In certain embodiments, the second intermediate has the formula:

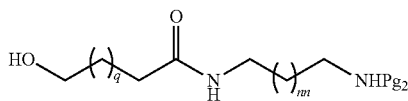

wherein q is from 1 to 4; and
nn is from 1 to 6.

In certain embodiments, the second intermediate is prepared by treating a cyclic compound having the formula:

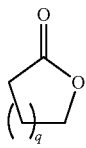

wherein q is from 1 to 4;
with a diamine compound having the formula:

isolating the crude product; and
treating the crude product with a reagent to protect the free amino group to provide the second intermediate.

In certain embodiments, q is 2. In certain embodiments, q is 3. In certain embodiments, nn is 1. In certain embodiments, q is 2 and nn is 1.

In certain embodiments, $Pg_2$ is carbobenzyloxy (CBz).

In certain embodiments, the second intermediate has the formula:

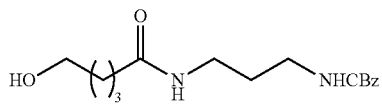

In certain embodiments, the functionalized ligand has the formula:

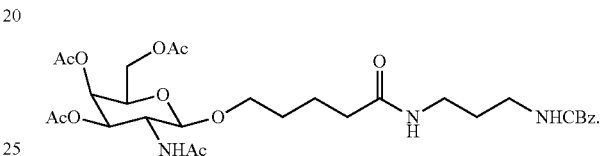

In certain embodiments, the pentafluorophenyl ester protected branching group and about 3.4 equivlaents of the functionalized ligand are dissolved in the organic solvent and $Pd(OH)_2/C$ is added under $H_2$ with stirring at room temperature until completion.

In certain embodiments, the organic solvent is acetonitrile, ethyl acetate, tetrahydrofuran or a mixture thereof. In certain embodiments, the organic solvent is tetrahydrofuran.

In certain embodiments, the reactive conjugate cluster is prepared without using column chromatography. In certain embodiments, the reactive conjugate cluster has the formula:

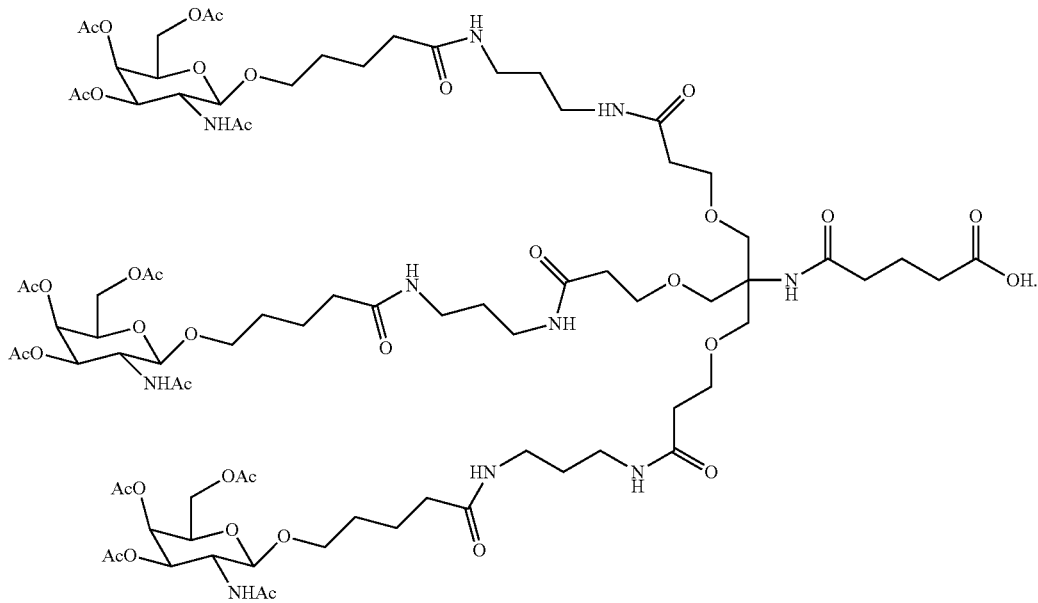 [SMILES: CC(=O)NC1C(OCCCCC(=O)NCCCNC(=O)CCOCC(COCCC(=O)NCCCNC(=O)CCCCOC2OC(COC(C)=O)C(OC(C)=O)C(OC(C)=O)C2NC(C)=O)(COCCC(=O)NCCCNC(=O)CCCCOC2OC(COC(C)=O)C(OC(C)=O)C(OC(C)=O)C2NC(C)=O)NC(=O)CCCC(=O)O)OC(COC(C)=O)C(OC(C)=O)C1OC(C)=O]

In certain embodiments, the reactive conjugate cluster has the formula:

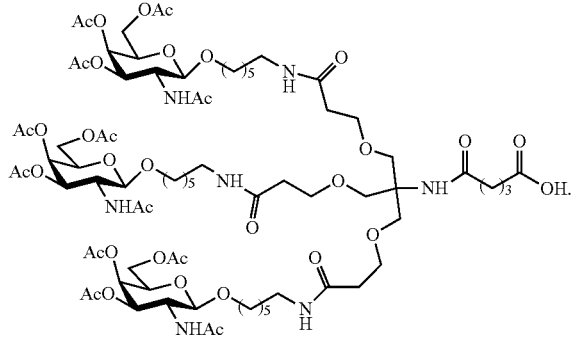

In certain embodiments, the reactive conjugate cluster has the formula:

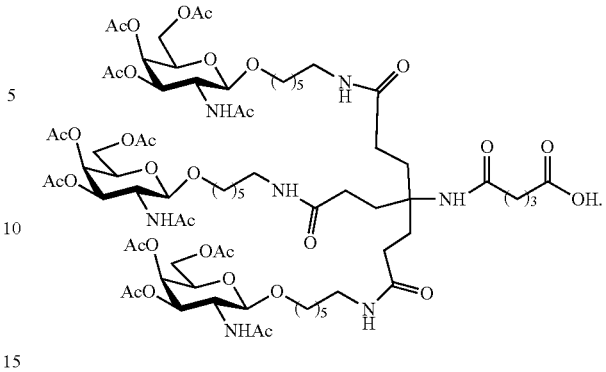

In certain embodiments, the instant methods further comprise treatment of the reactive conjugate cluster with pentafluorophenyl trifluoroacetate to provide PFP esterified conjugate cluster. In certain embodiments, the PFP esterified conjugate cluster is prepared without using column chromatography. In certain embodiments, the PFP esterified conjugate cluster is purified by precipitation. In certain embodiments, the PFP esterified conjugate cluster is prepared by treatment of the reactive conjugate cluster with pentafluorophenyl trifluoroacetate in dichloromethane.

In certain embodiments, the PFP esterified conjugate cluster has the formula:

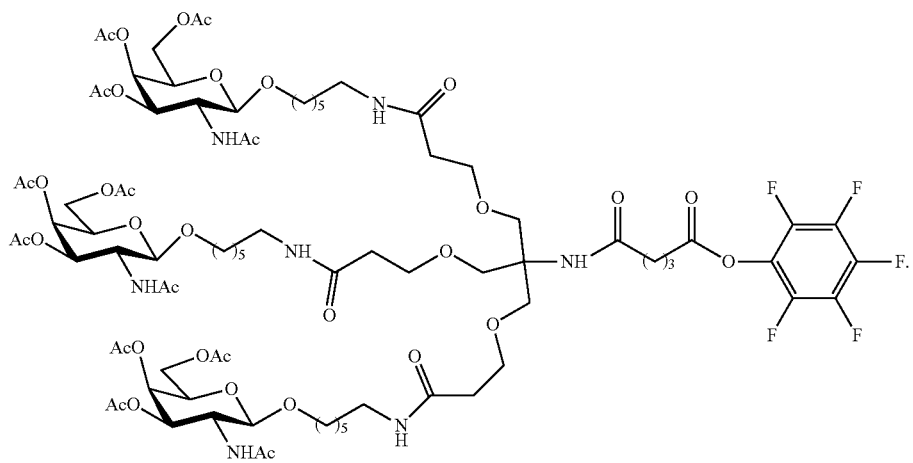

In certain embodiments, the PFP esterified conjugate cluster has the formula:

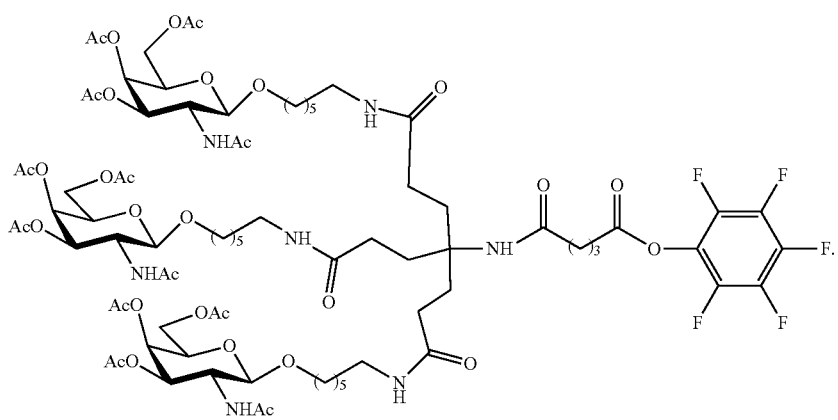

In certain embodiments, methods are provided for the synthesis of a reactive conjugate clusters having the formula:

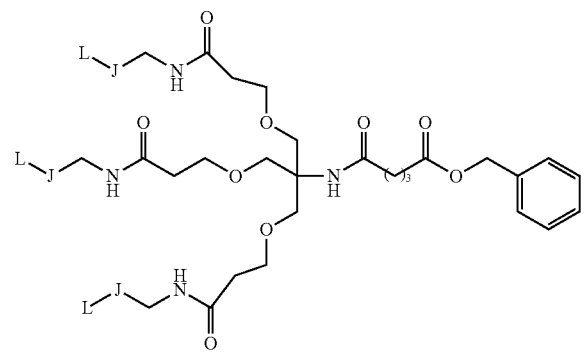

wherein:

J is $C_2$ to $C_9$ alkyl optionally interrupted with one or more groups selected from —O—, —N(H)— and C(=O); and L is an optionally protected ligand;

comprising treatment of a compound having the formula:

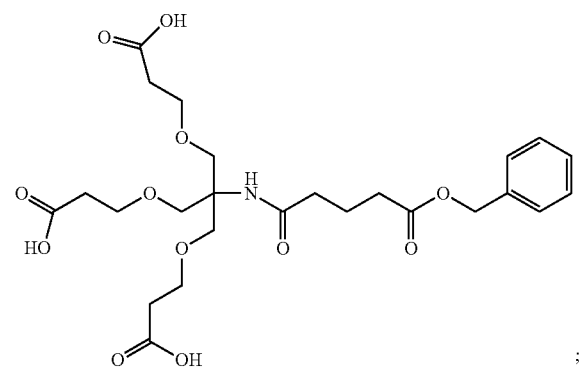 [SMILES: O=C(O)CCOCC(COCCC(=O)O)(COCCC(=O)O)NC(=O)CCCC(=O)OCc1ccccc1]

with a compound having the formula:

L-J-CH$_2$—NH$_2$;

under conditions to provide to provide the reactive conjugate cluster.

In certain embodiments, each L has the formula:

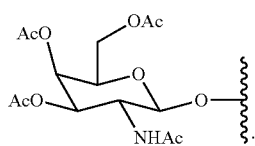 [SMILES: *OC1OC(COC(C)=O)C(OC(C)=O)C(OC(C)=O)C1NC(C)=O]

In certain embodiments, each J is $C_3$ to $C_7$ alkyl. In certain embodiments, each J is $C_4$ to $C_8$ alkyl interrupted with one amide group (—N(H)—C(=O)—).

In certain embodiments, L-J-CH$_2$—NH$_2$ has the formula:

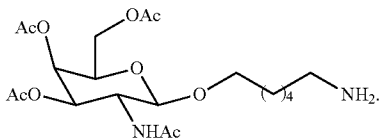

In certain embodiments, L-J-CH$_2$—NH$_2$ has the formula:

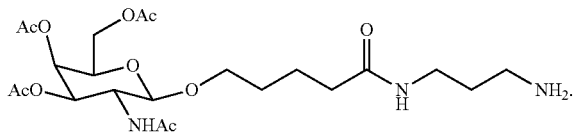 [SMILES: CC(=O)NC1C(OCCCCC(=O)NCCCN)OC(COC(C)=O)C(OC(C)=O)C1OC(C)=O]

In certain embodiments, methods are provided for the synthesis of a reactive conjugate cluster having the formula:

(L-A-N(H)C(=O)-E-)$_m$-Bg$_a$ wherein:

L is a ligand;

A is $C_2$ to $C_{10}$ alkyl optionally interrupted with one or more groups selected from —O—, —N(H)— and C(=O);

E is a single bond or $C_1$ to $C_{10}$ alkyl optionally interrupted with one or more groups selected from —O—, —N(H)— and C(=O);

Bg$_a$ is a reactive branching group;

m is from 2 to about 6;

comprising:

reacting a pentafluorophenyl ester protected branching group having the formula:

(PFP—O—C(=O)-E-)$_m$-Bg$_a$;

with at least m equivalents of a functionalized ligand having the formula:

L-A-N(H)Pg$_2$ wherein Pg$_2$ is an amino protecting group;

in an organic solvent with a palladium catalyst and H$_2$ for a time and under conditions sufficient to provide the reactive conjugate cluster.

In certain embodiments, each E is $C_1$ to $C_4$ alkyl. In certain embodiments, each E is CH$_2$. In certain embodiments, each E is a single bond.

In certain embodiments, the reactive branching group has the formula:

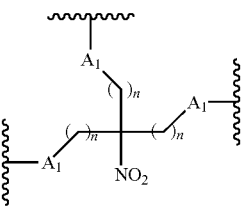

wherein:

each A$_1$ is, independently, CH$_2$, O or N(H); and each n is, independently, 1 or 2.

In certain embodiments, the reactive branching group has the formula:

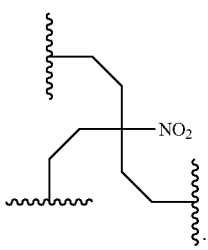 [SMILES: *CCC(CC*)(CC*)[N+](=O)[O-]]

In certain embodiments, the reactive branching group has the formula:

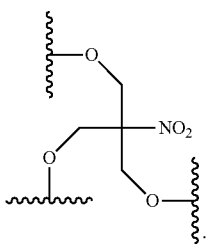 [SMILES: *OCC(CO*)(CO*)[N+](=O)[O-]]

In certain embodiments, m is 3.

In certain embodiments, the pentafluorophenyl ester protected branching group has the formula:

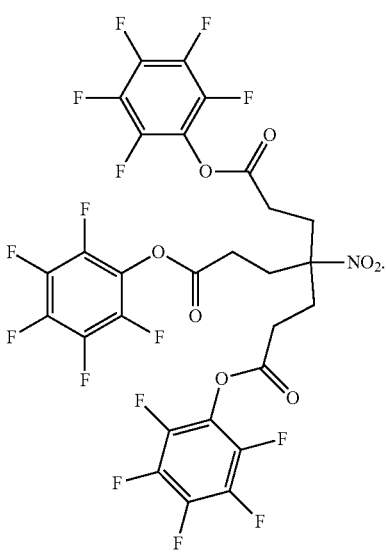 [SMILES: O=C(CCC(CCC(=O)Oc1c(F)c(F)c(F)c(F)c1F)(CCC(=O)Oc1c(F)c(F)c(F)c(F)c1F)[N+](=O)[O-])Oc1c(F)c(F)c(F)c(F)c1F]

In certain embodiments, the pentafluorophenyl ester protected branching group is at least about 95% pure.

In certain embodiments, each L has the formula:

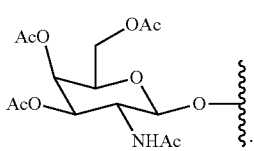 [SMILES: *OC1OC(COC(C)=O)C(OC(C)=O)C(OC(C)=O)C1NC(C)=O]

In certain embodiments, the functionalized ligand has the formula:

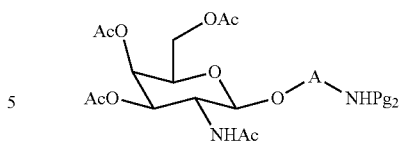

wherein

A is $C_2$ to $C_{10}$ alkyl optionally interrupted with one or more groups selected from —O—, —N(H)— and C(=O);

$Pg_2$ is an amino protecting group. In certain embodiments, the functionalized ligand is prepared by treating a first intermediate having the formula:

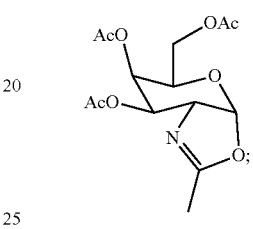

with a second intermediate having the formula:

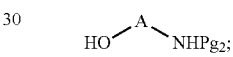

for a time and under conditions to provide the functionalized ligand; and wherein the first intermediate is prepared in situ by treatment of the protected galactose sugar having the formula:

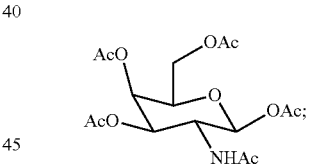

in an organic solvent with trimethylsilyl triflate (TMSOTf).

In certain embodiments, each A is $C_4$ to $C_8$ alkyl. In certain embodiments, A is $C_4$ to $C_8$ alkyl interrupted with one amide group (—N(H)—C(=O)—).

In certain embodiments, the second intermediate has the formula:

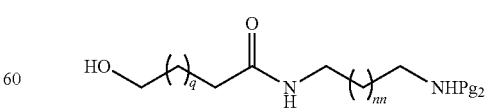

wherein q is from 1 to 4; and nn is from 1 to 6. In certain embodiments, the second intermediate is prepared by treating a cyclic compound having the formula:

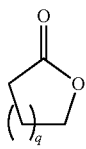

wherein q is from 1 to 4;
with a diamine compound having the formula:

isolating the crude product; and
treating the crude product with a reagent to protect the free amino group to provide the second intermediate.

In certain embodiments, q is 2. In certain embodiments, q is 3.

In certain embodiments, nn is 1.

In certain embodiments, q is 2 and nn is 1.

In certain embodiments, $Pg_2$ is carbobenzyloxy (CBz).

In certain embodiments, the second intermediate has the formula:

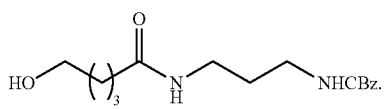

In certain embodiments, the functionalized ligand has the formula:

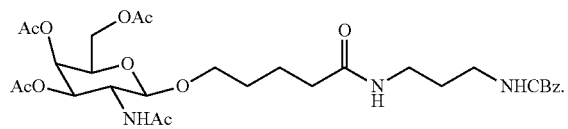

In certain embodiments, the functionalized ligand has the formula:

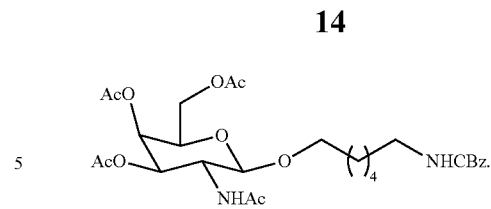

In certain embodiments, the pentafluorophenyl ester protected branching group and about 3.1 equivalents of the functionalized ligand are dissolved in the organic solvent and $Pd(OH)_2/C$ is added under $H_2$ with stirring at room temperature until completion.

In certain embodiments, the organic solvent is acetonitrile, ethyl acetate, tetrahydrofuran, methanol or a mixture thereof. In certain embodiments, the organic solvent is a mixture of ethyl acetate and methanol.

In certain embodiments, the reactive conjugate cluster is prepared without using column chromatography. In certain embodiments, the reactive conjugate cluster has the formula:

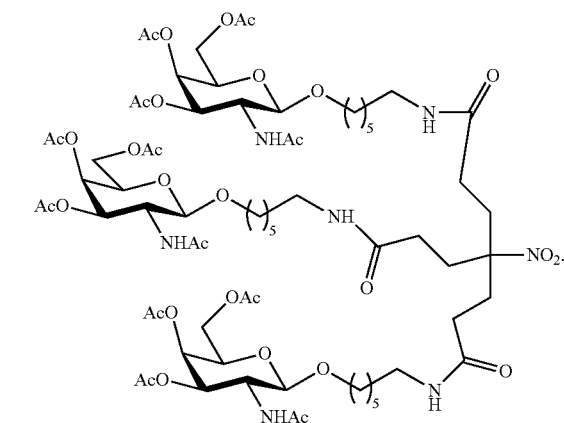

In certain embodiments, the methods provided herein further include treatment of the reactive conjugate cluster under conditions to provide the PFP esterified conjugate cluster.

In certain embodiments, the PFP esterified conjugate cluster is prepared without using column chromatography. In certain embodiments, the PFP esterified conjugate cluster is purified by precipitation. In certain embodiments, the PFP esterified conjugate cluster has the formula:

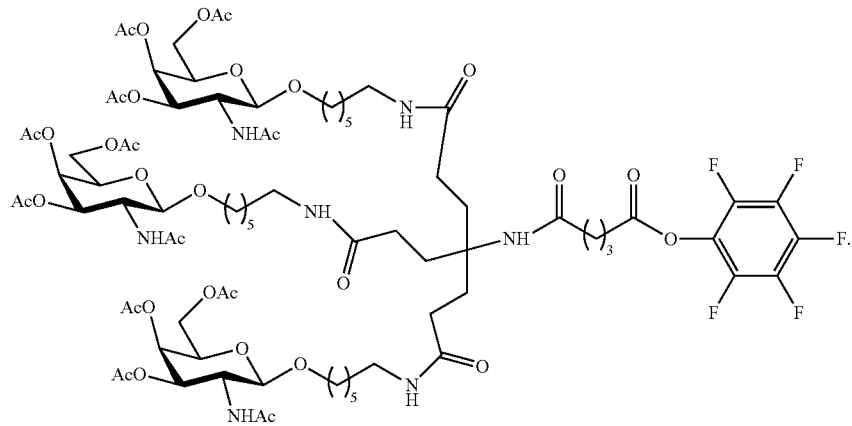

DETAILED DESCRIPTION OF THE INVENTION

Provided herein are improved methods for preparing reactive conjugate clusters and intermediates used in such methods. The methods include the preparation of ligand intermediates that are useful for covalently attaching to a branching group. The branching groups are orthogonally protected to provide reactive sites for attachment of the ligand intermediates and a reactive site for covalent attachment to a parent compound such as an oligomeric compound after the reactive conjugate cluster has been prepared. The present methods provide reactive conjugate clusters in fewer steps with higher purity compared to previously reported methods. In certain embodiments, the present methods provide improved purity by eliminating certain impurities such as for example transacylation impurities that are formed using existing methods. The improved methods also provide an increase in overall yield and a cost benefit over existing methods.

Reactive conjugate clusters as provided herein comprise at least two ligands that are each tethered to a branching group which includes or is covalently attached to a reactive group for forming a covalent linkage to a parent compound. Reactive conjugate clusters can be reacted with a reactive group on a parent compound to covalently attach the conjugate cluster to the parent compound. Reactive conjugate clusters are generally prepared with reactive groups protected which can be deprotected in the final conjugated parent compound. One example of a reactive conjugate cluster is a carbohydrate cluster wherein the ligand groups are carbohydrates such as galactose or a protected galactose.

In certain embodiments, reactive conjugate clusters as provided herein have the structure:

[Ligand-tether]$_x$-branching group-G-H

Functional groups on the ligand are generally protected. The x is from 2 to about 6 and G is a reactive group for linking the reactive conjugate cluster via a conjugate linker to a parent compound. In certain embodiments, x is 3. In certain embodiments, G includes a partial linker group and the other portion of the linker group is provided by the parent compound. In certain embodiments, G is a single bond. In certain embodiments, G is a reactive conjugate linker.

In certain embodiments, reactive conjugate clusters as provided herein have the structure:

[Ligand-tether]$_x$-Bg$_a$

Functional groups on the ligand are generally protected. The x is from 2 to about 6 and Bg$_a$ is a reactive branching group comprising a group that is reactive with another functional group to facilitate attachment of the conjugate cluster to a parent compound such as an oligomeric compound. In certain embodiments Bg$_a$ comprises a NO$_2$ group that is reactive with another functional group to facilitate attachment of the conjugate cluster to a parent compound such as an oligomeric compound. In certain embodiments Bg$_a$ comprises a NO$_2$ group that is reactive with a reactive conjugate linker to facilitate attachment of the conjugate cluster to a parent compound such as an oligomeric compound.

In certain embodiments, a reactive conjugate cluster comprises a branching group with three tethered carbohydrate ligands and a further group that provides a reactive group for forming a linker to a parent compound. One representative example of a reactive conjugate cluster as provided herein has the structure:

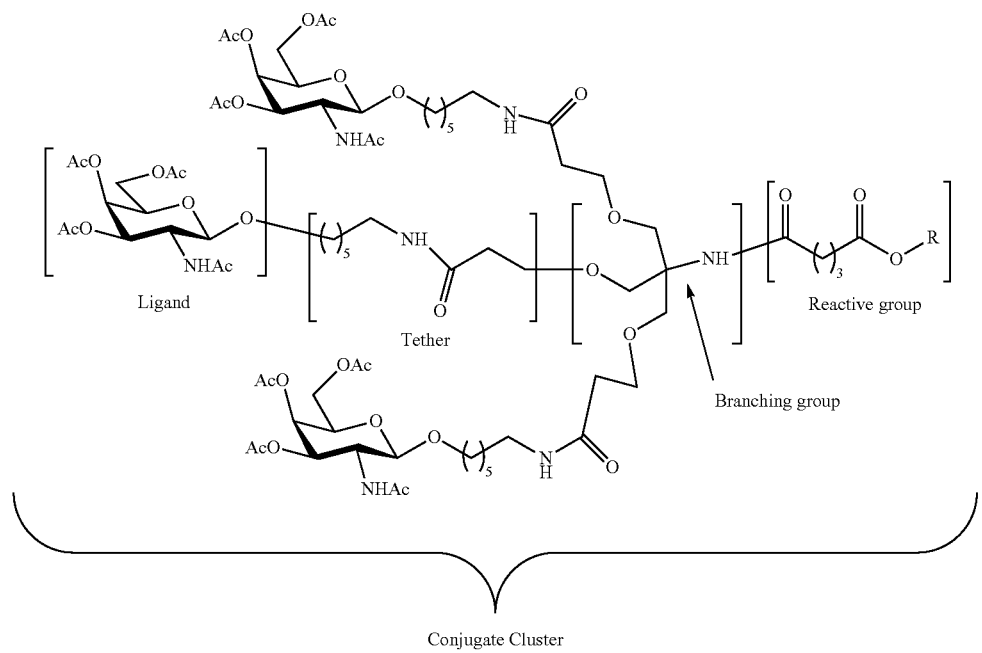

wherein R is H, pentafluorophenyl or other group for forming a covalent linkage to a parent compound.

In certain embodiments, a reactive conjugate cluster comprises a branching group with three tethered carbohydrate ligands and a further group that provides a reactive group for forming a linker to a parent compound. One representative example of a reactive conjugate cluster as provided herein has the structure:

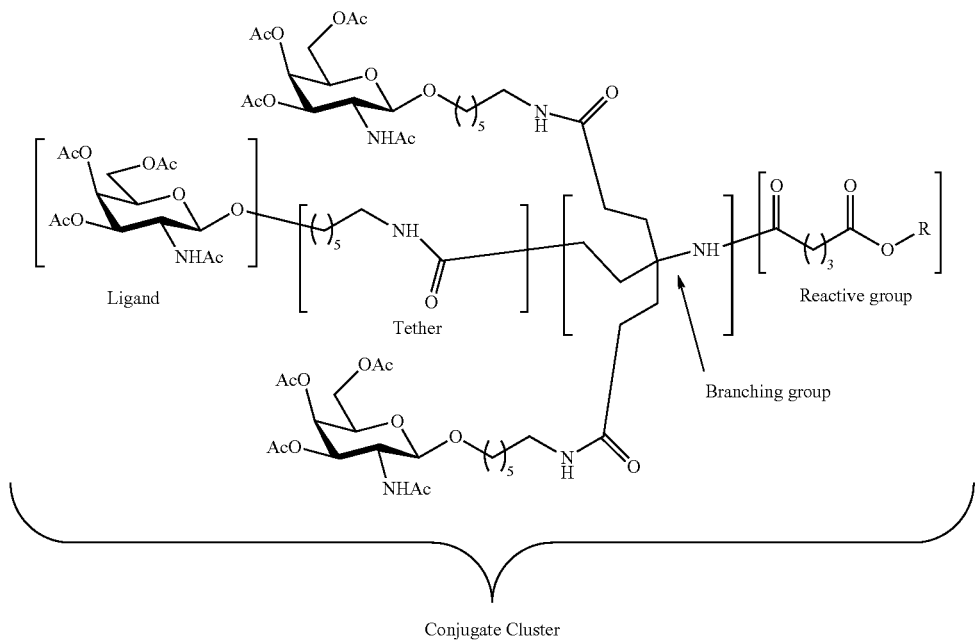

wherein R is H, pentafluorophenyl or other group for forming a covalent linkage to a parent compound.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

As used herein, "conjugate" or "conjugate group" means an atom or group of atoms capable of being bound to a parent compound such as an oligonucleotide or an oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. In certain embodiments, a conjugate group comprises a reactive conjugate cluster.

As used herein, "carbohydrate cluster" means a compound having two or more carbohydrate residues attached to a scaffold or linker group (referred to herein as a branching group). (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetyl-galactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates. In certain embodiments, a carbohydrate cluster comprises a reactive conjugate cluster.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, a carbohydrate cluster can be covalently attached to a parent compound to enhance one or more properties of the parent compound. As used herein, "parent compound" means a small molecule, a large molecule or a polymer capable of having a carbohydrate cluster attached thereto. In certain embodiments, the parent compound is a drug such as a naturally occurring or synthetic small molecule, a naturally occurring or synthetic large molecule, or a naturally occurring or synthetic polymer. In certain embodiments, a parent compound is a naturally occurring or synthetic peptide or a naturally occurring or synthetic nucleic acid molecule. In certain embodiments, a parent compound is an oligomeric compound or an oligonucleotide.

As used herein, "conjugate linker" or "linker" in the context of a conjugate group means a portion of a conjugate group comprising any atom or group of atoms and which covalently link the conjugate group to a parent compound such as an oligomeric compound or an antisense oligonucleotide. In certain embodiments, a conjugate group is attached directly to a parent compound without a linker group (the branching group is attached to the parent compound directly).

Conjugate groups have at least one reactive group for forming covalent attachment to a parent compound such as an oligomeric compound or an antisense oligonucleotide. In certain embodiments, the point of attachment on the oligomeric compound is the 3'-oxygen atom of the 3'-hydroxyl group of the 3' terminal nucleoside of the oligomeric compound. In certain embodiments the point of attachment on the oligomeric compound is the 5'-oxygen atom of the 5'-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, reactive conjugate clusters as provided herein are attached to a parent compound such that the attachment includes a cleavable moiety (e.g., a cleavable bond or cleavable nucleoside). As used herein, "cleavable bond" means any chemical bond capable of being split. In certain embodiments, a cleavable bond is selected from among: an amide, a polyamide, an ester, an ether, a phosphodiester, a phosphate ester, a carbamate, a di-sulfide, or a peptide.

In certain embodiments, reactive conjugate clusters as prepared herein are attached via a cleavable moiety to a parent compound. In certain embodiments, a cleavable moiety is a cleavable bond. In certain embodiments, a cleavable moiety comprises a cleavable bond. In certain such embodiments, the cleavable moiety attaches to an antisense oligonucleotide. In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester linkage. In certain embodiments, the cleavable moiety is 2'-deoxy adenosine that is attached to the 5' position of the antisense oligonucleotide by a phosphodiester linkage and is attached to the linker by a phosphodiester or phosphorothioate linkage. In certain embodiments, the cleavable moiety is 2'-deoxy adenosine that is attached to the 5' position of the antisense oligonucleotide by a phosphodiester linkage and is attached to the linker by a phosphodiester linkage.

In certain embodiments, the cleavable moiety is attached to the 3' position of the antisense oligonucleotide. In certain embodiments, the cleavable moiety is attached to the 5' position of the antisense oligonucleotide. In certain embodiments, the cleavable moiety is attached to a 2' position of the antisense oligonucleotide. In certain embodiments, the cleavable moiety is attached to the antisense oligonucleotide by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage. In certain embodiments, the conjugate group does not include a cleavable moiety.

In certain embodiments, a cleavable moiety has a structure selected from among the following:

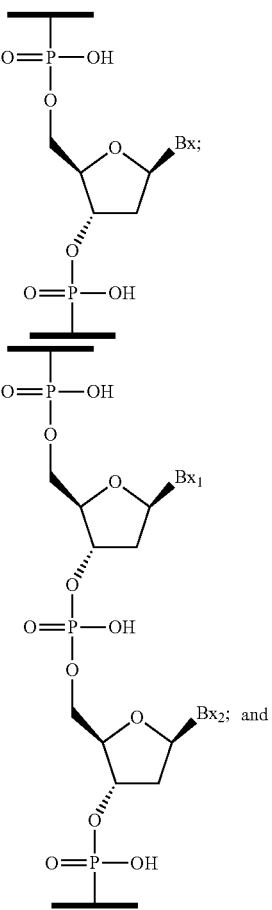

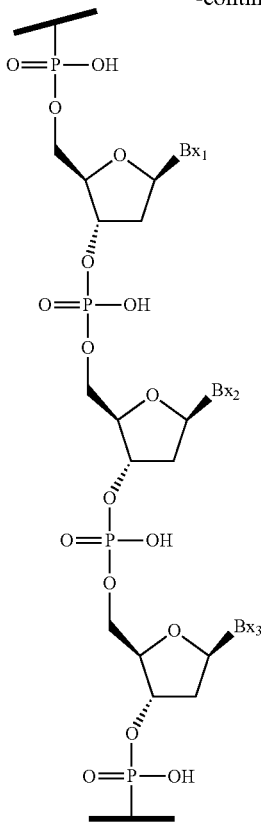

wherein each of Bx, Bx$_1$, Bx$_2$, and Bx$_3$ is independently a heterocyclic base moiety. In certain embodiments, the cleavable moiety has a structure selected from among the following:

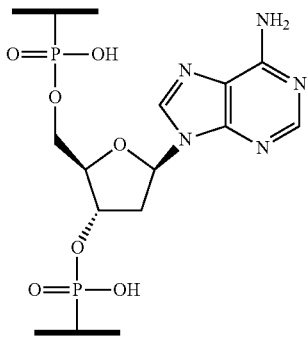

In certain embodiments, reactive conjugate clusters as provided herein comprise a linker. In certain such embodiments, the linker is covalently bound to the cleavable moiety. In certain such embodiments, the linker is covalently bound to a parent compound such as an oligomeric compound. In certain embodiments, the linker further comprises a covalent attachment to a solid support. In certain embodiments, the linker further comprises a covalent attachment to a protein binding moiety. In certain embodiments, the linker further comprises a covalent attachment to a solid support and further comprises a covalent attachment to a protein binding moiety. In certain embodiments, the linker includes multiple positions for attachment of tethered ligands. In certain embodiments, the linker further comprises one or more cleavable bond. In certain embodiments, the reactive conjugate cluster does not include a linker.

In certain embodiments, the linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense oligonucleotide. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl.
In certain embodiments, a linker has a structure selected from among:
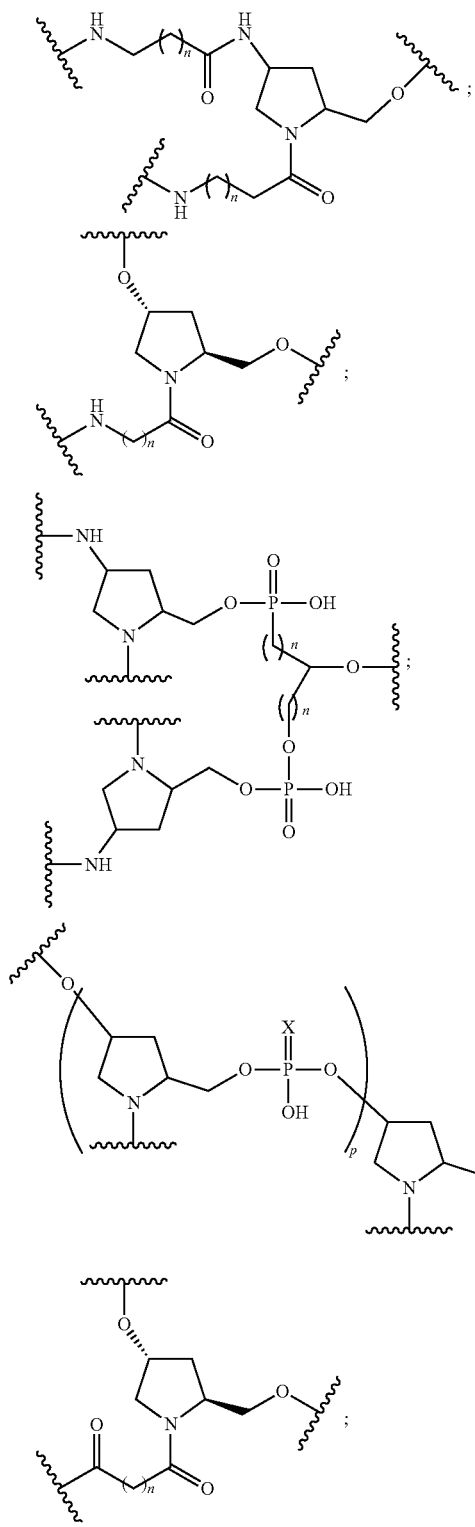
-continued
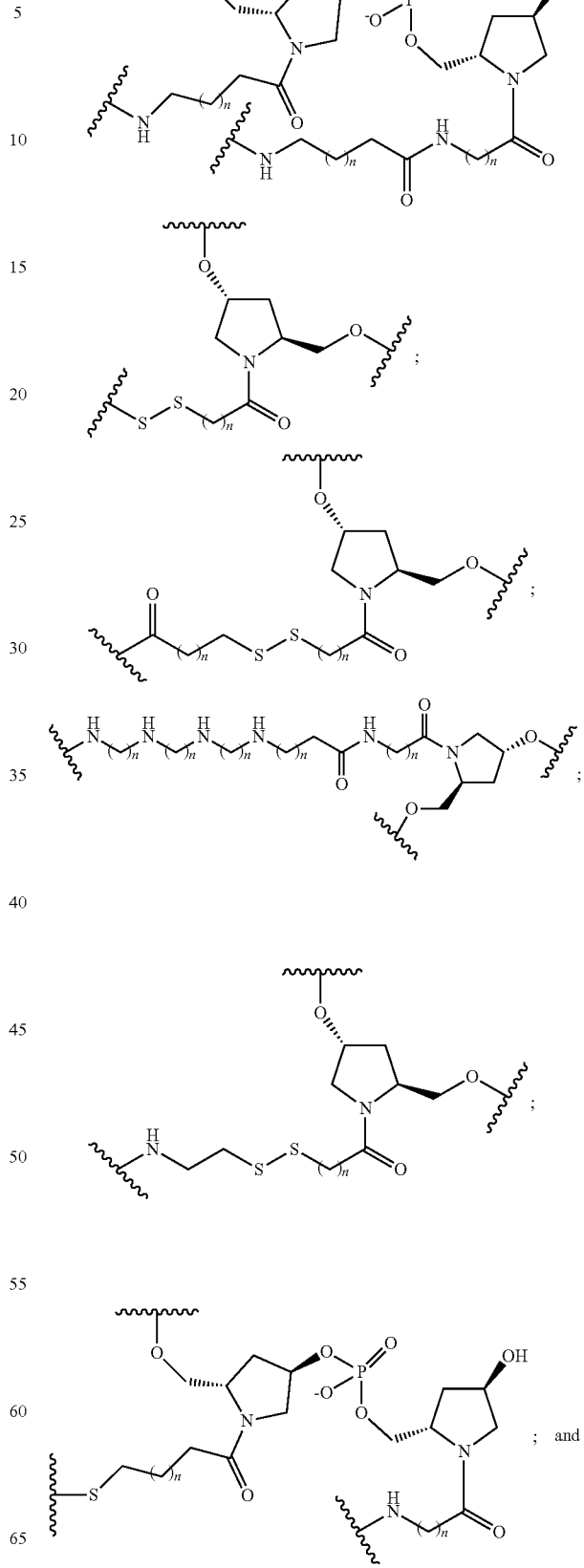

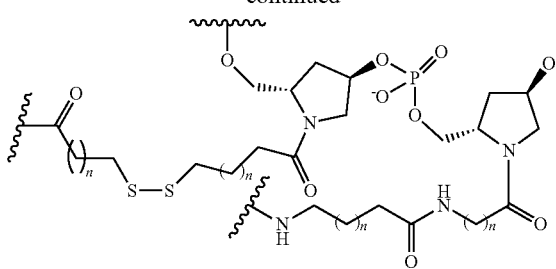
wherein each n is, independently, from 1 to 20; and p is from 1 to 6.
In certain embodiments, a linker has a structure selected from among:
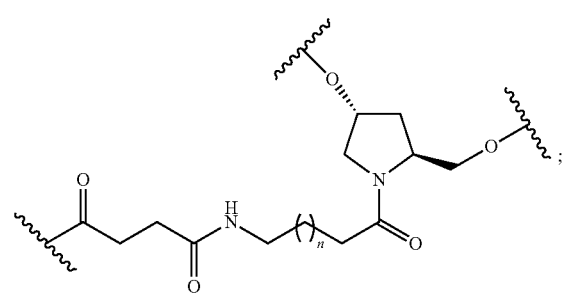
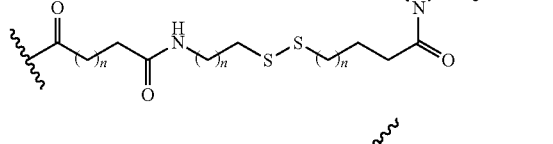
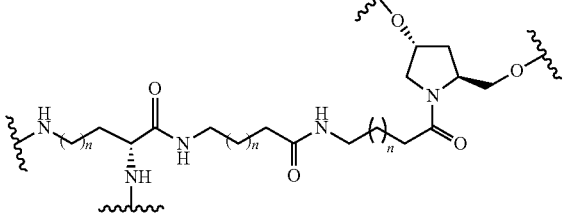
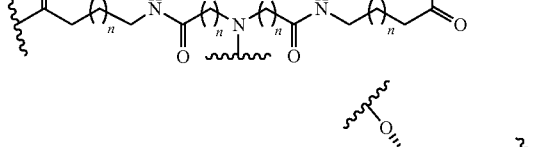
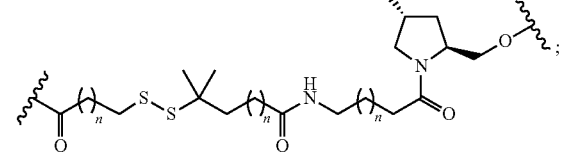
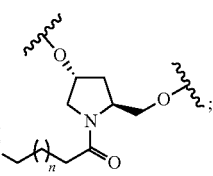
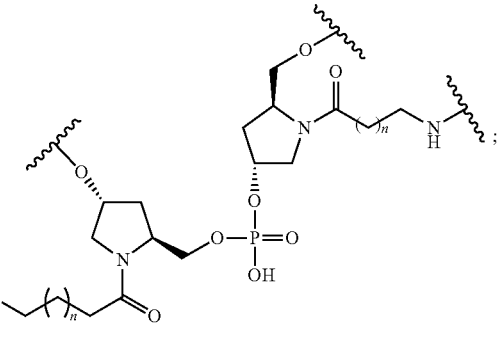
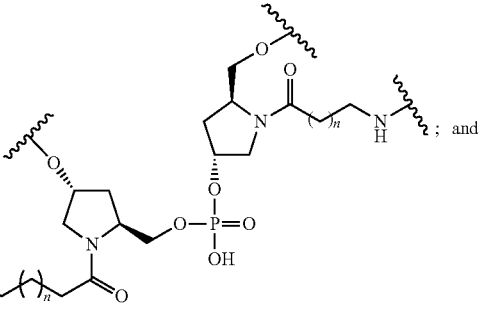
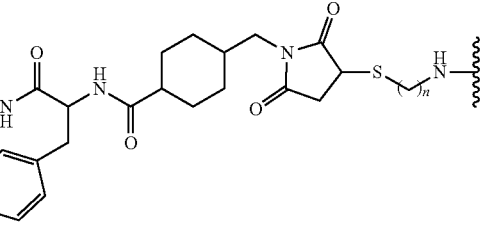
wherein each n is, independently, from 1 to 20.
In certain embodiments, a linker has a structure selected from among:
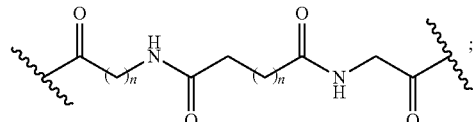
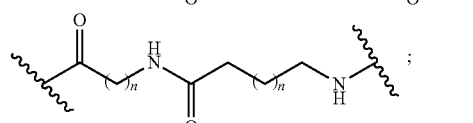
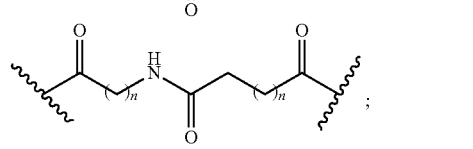

-continued
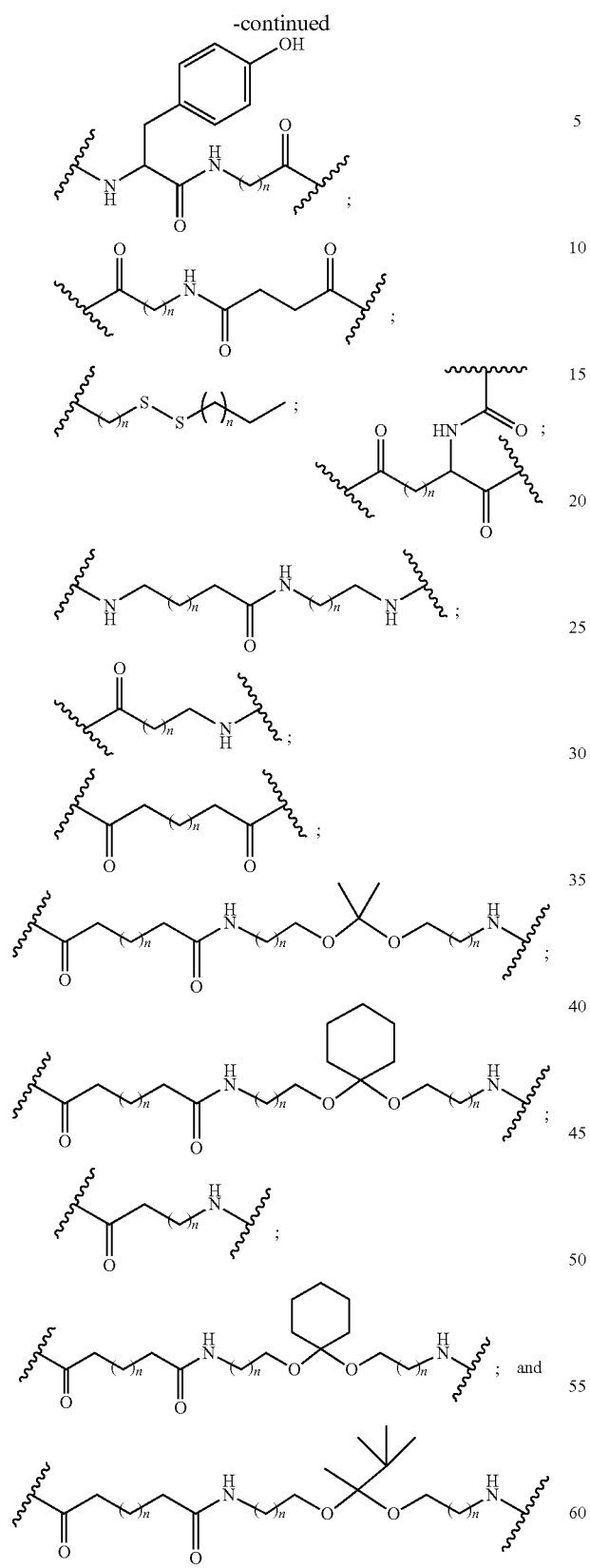
wherein n is from 1 to 20.
In certain embodiments, a linker has a structure selected from among:
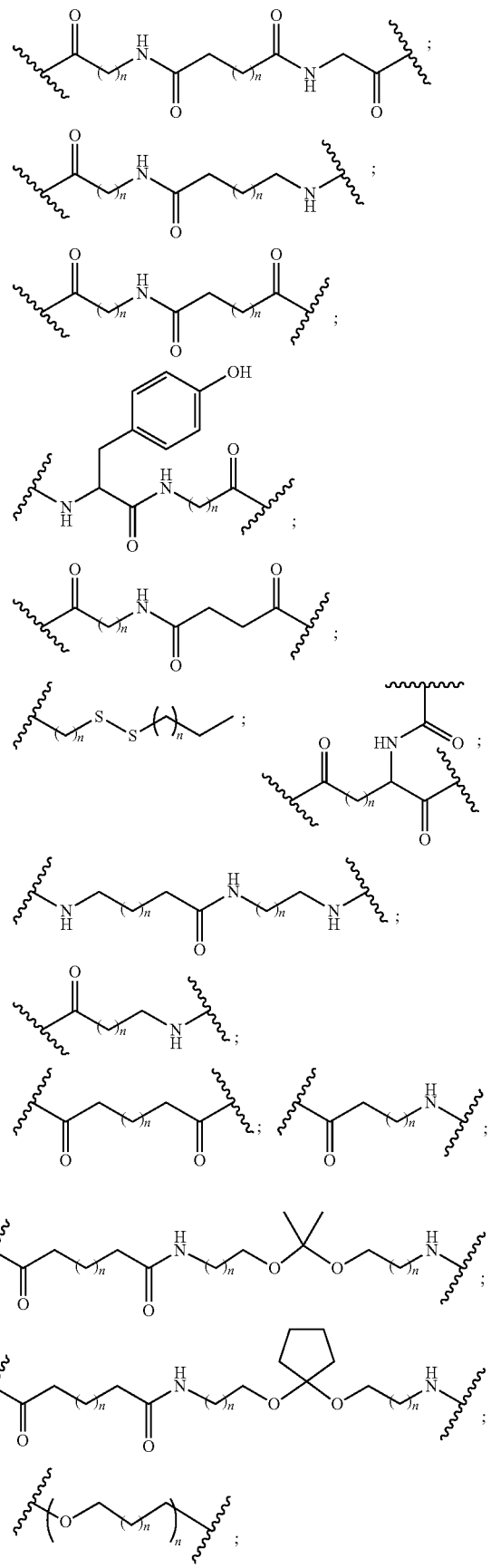

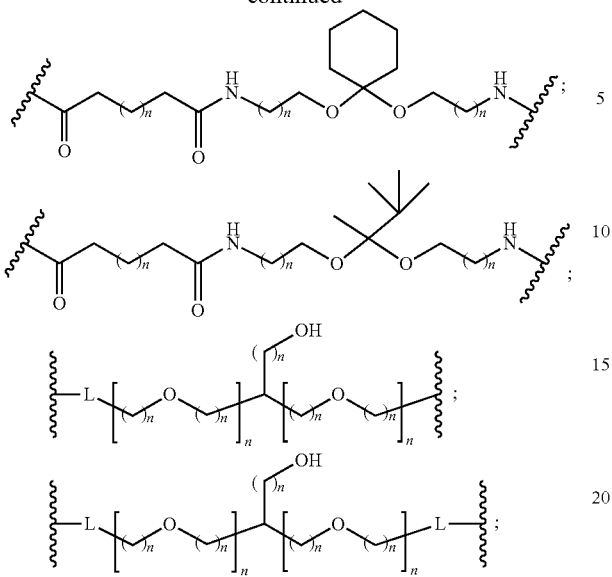
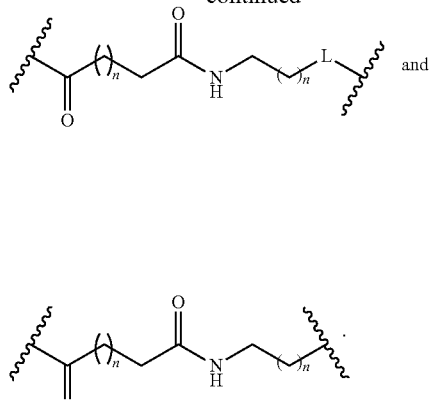
wherein each L is, independently, a phosphorus linking group or a neutral linking group; and each n is, independently, from 1 to 20.
In certain embodiments, a linker has a structure selected from among:
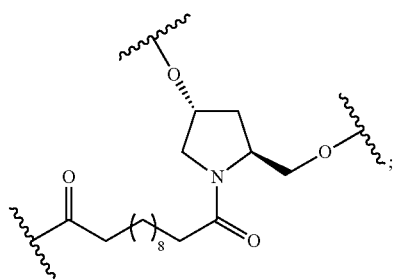
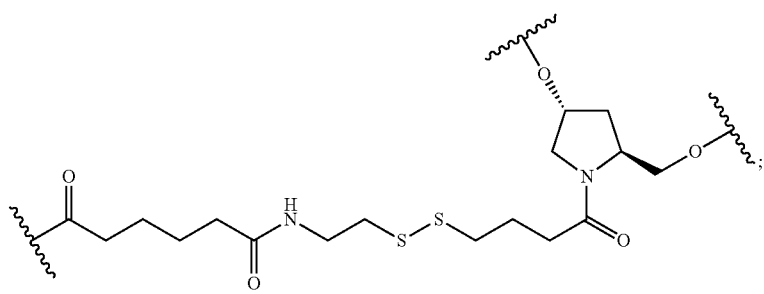
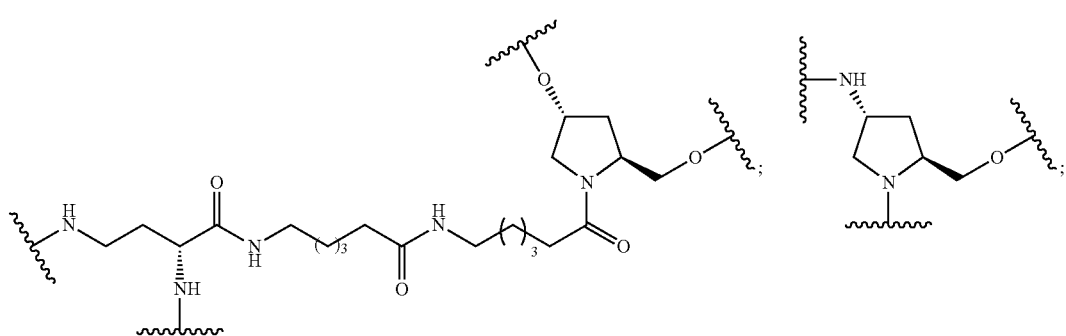

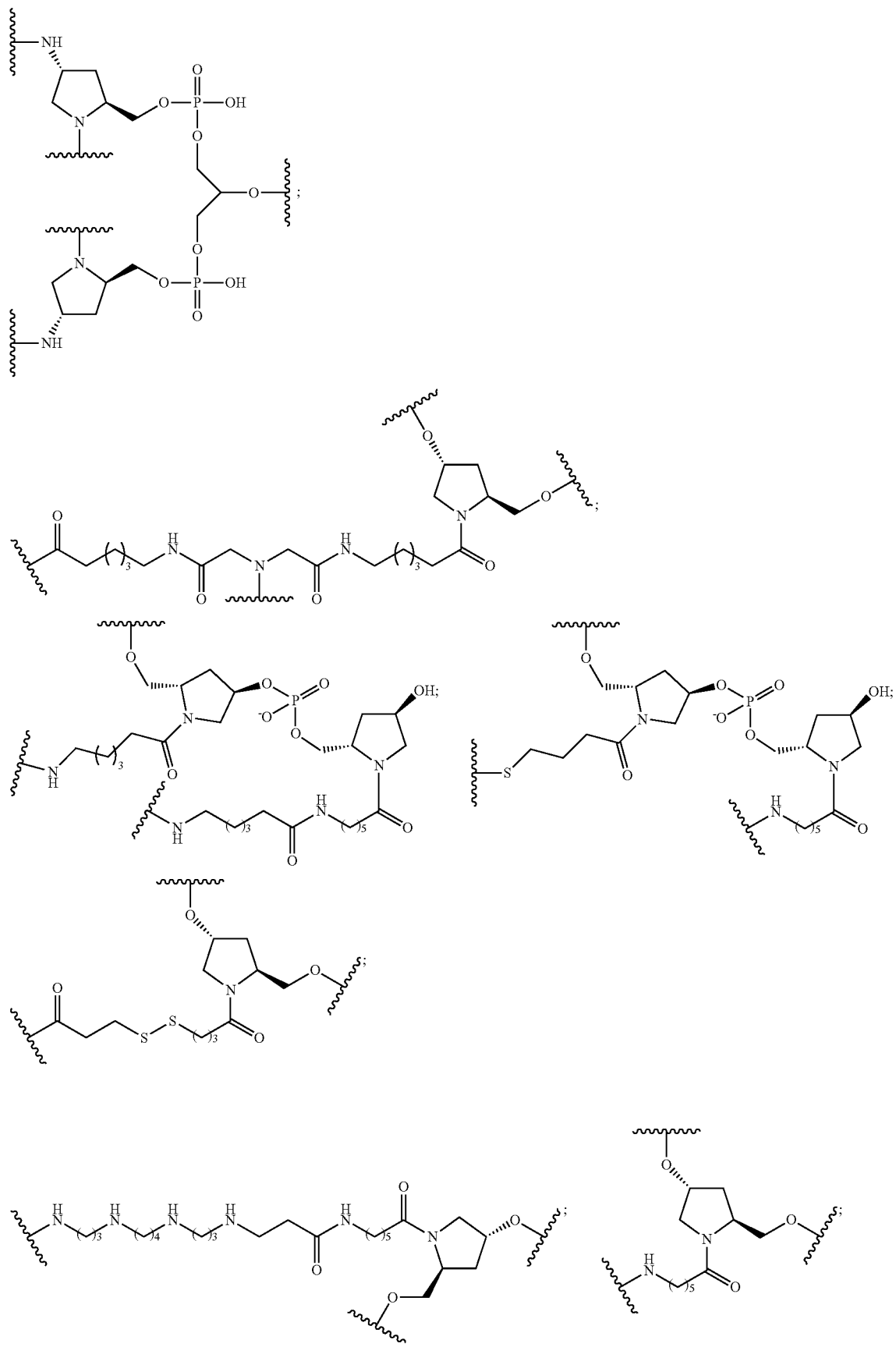

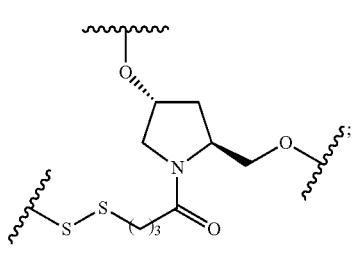
-continued
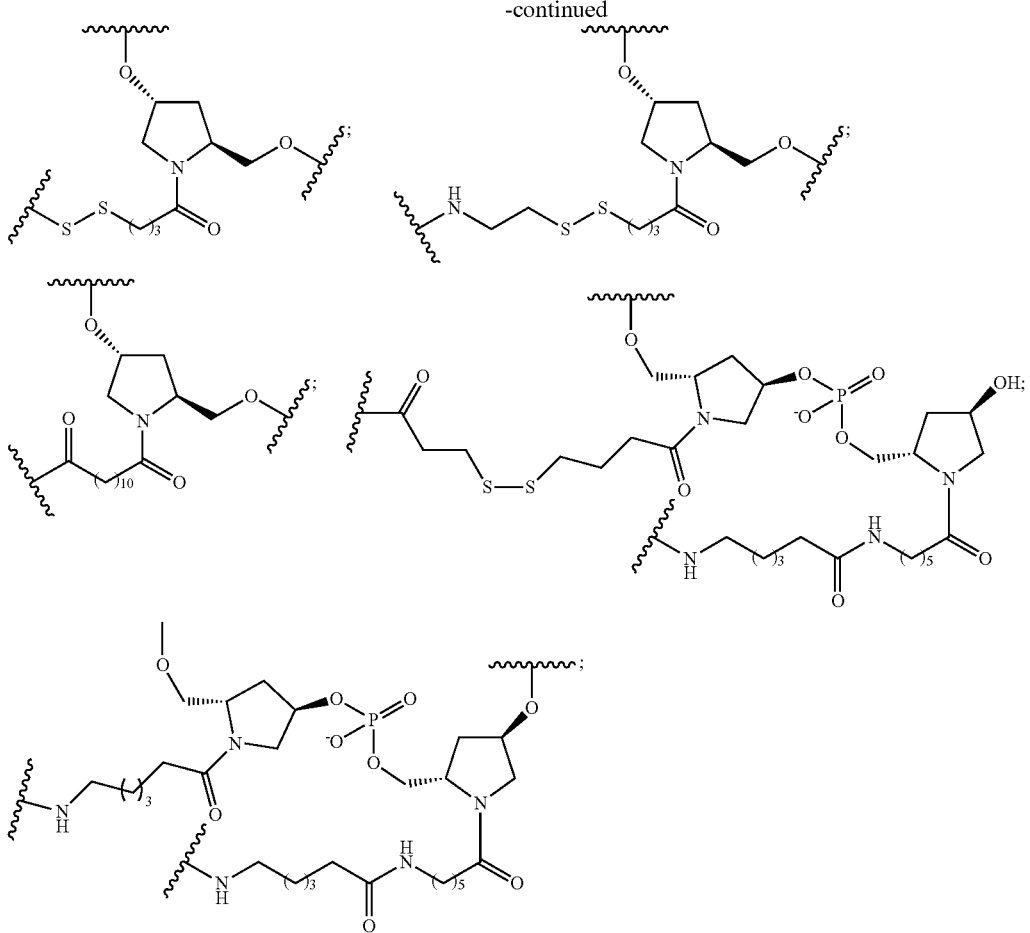
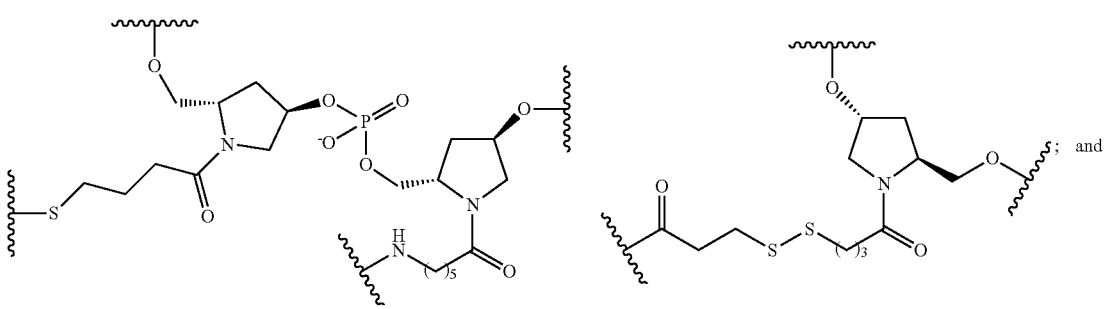
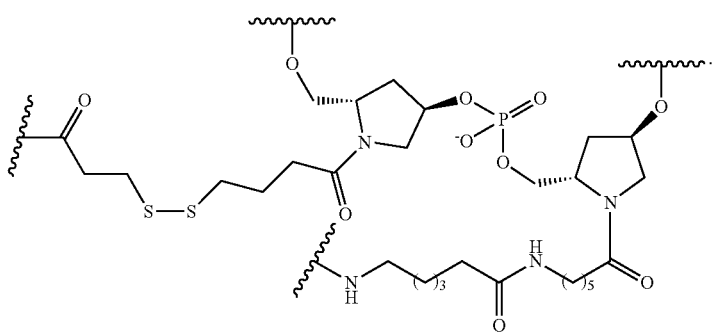

In certain embodiments, a linker has a structure selected from among:
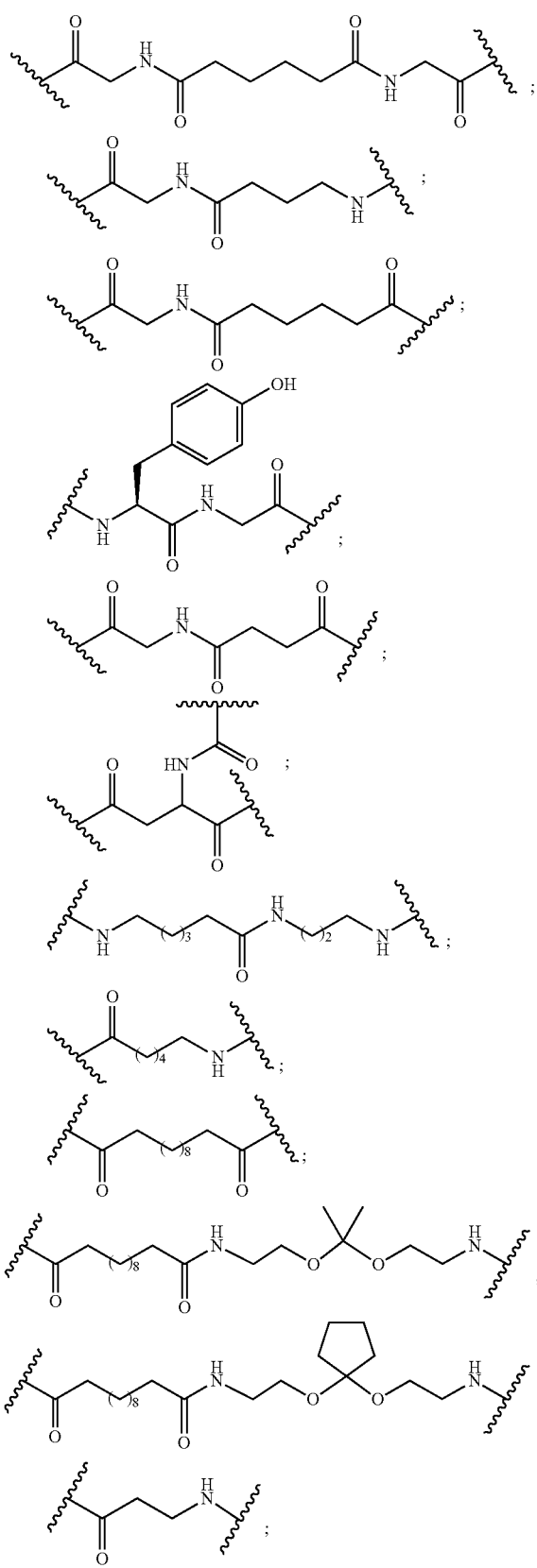
-continued
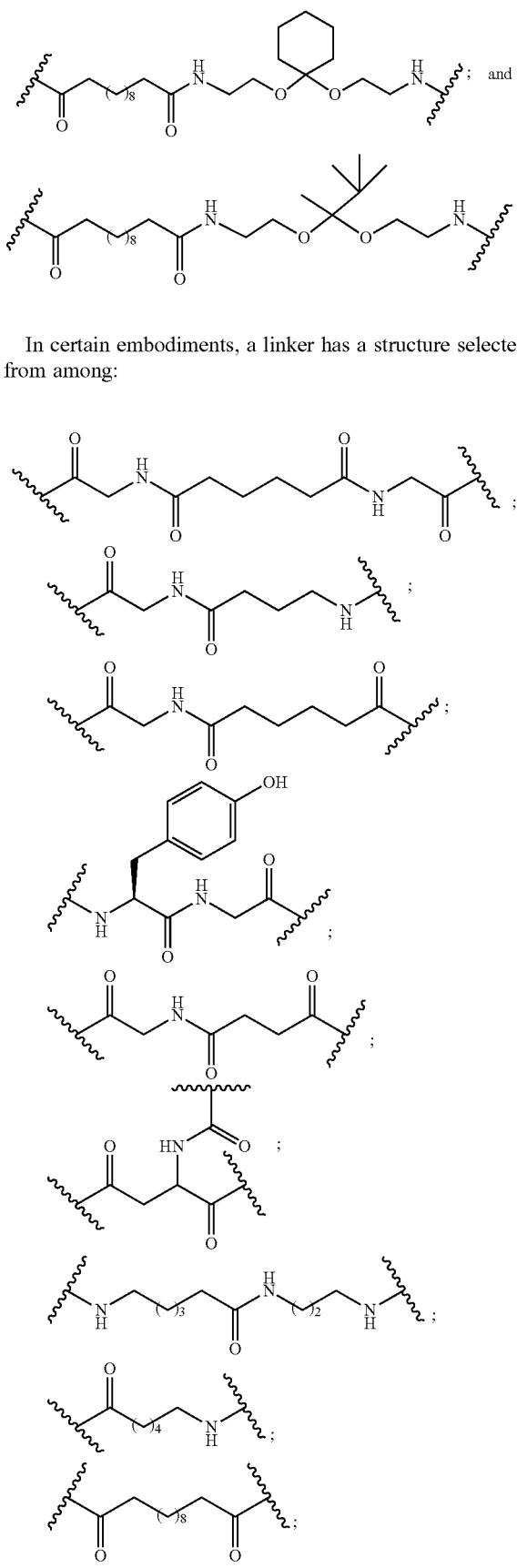
In certain embodiments, a linker has a structure selected from among:

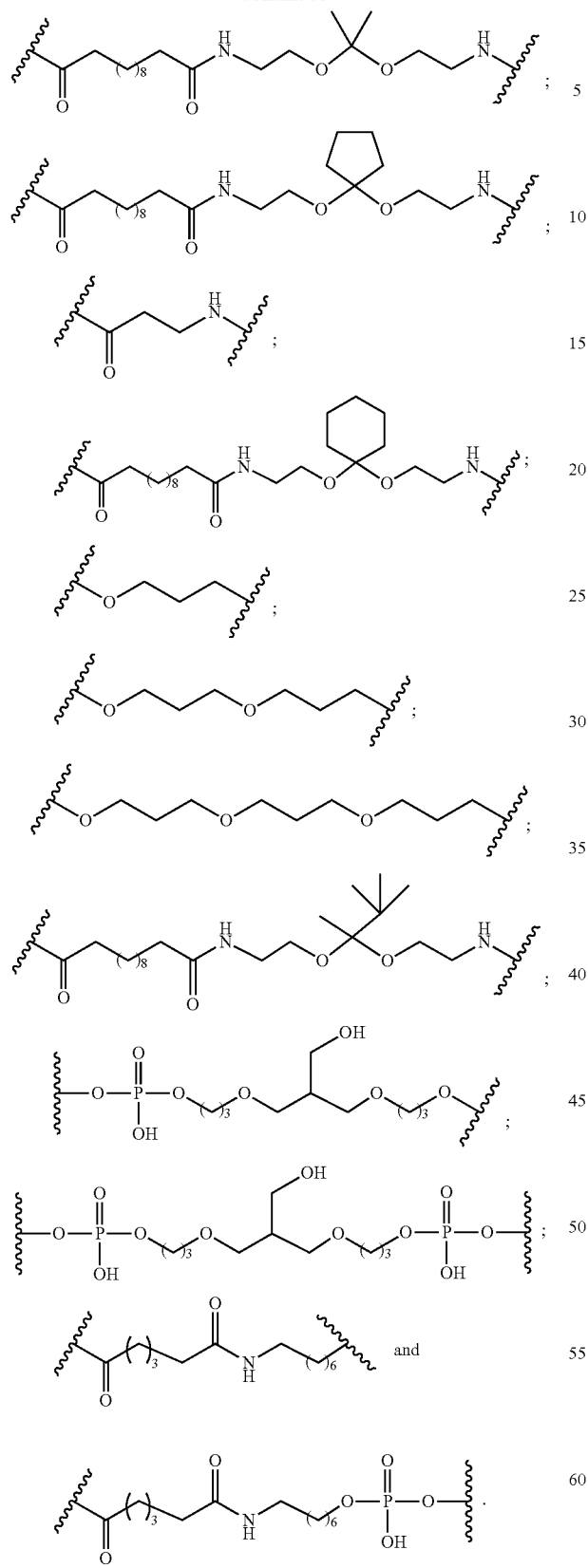
wherein n is from 1 to 20.
In certain embodiments, a linker has a structure selected from among:
In certain embodiments, a linker has a structure selected from among:
In certain embodiments, the conjugate linker has the structure:

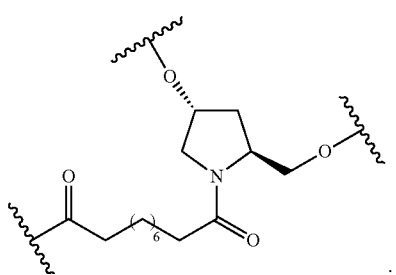
In certain embodiments, a linker has a structure selected from among:
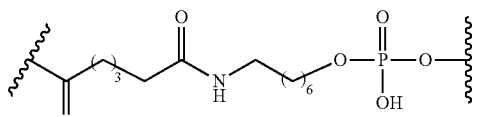
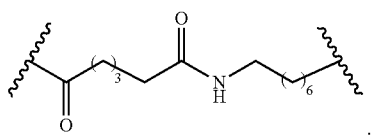
and
In certain embodiments, a linker has a structure selected from among:
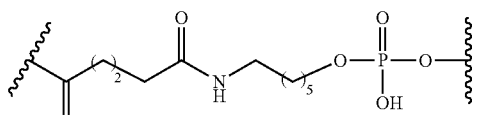
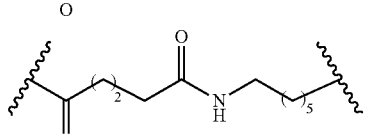
and
In certain embodiments, a linker has a structure selected from among:
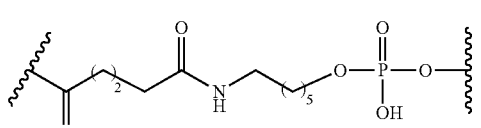
In certain embodiments, a branching group has a structure selected from among:
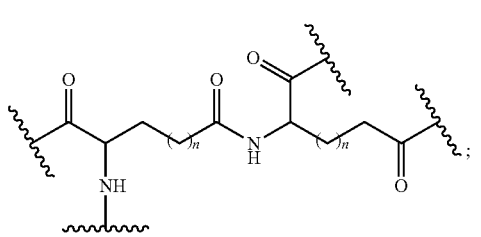
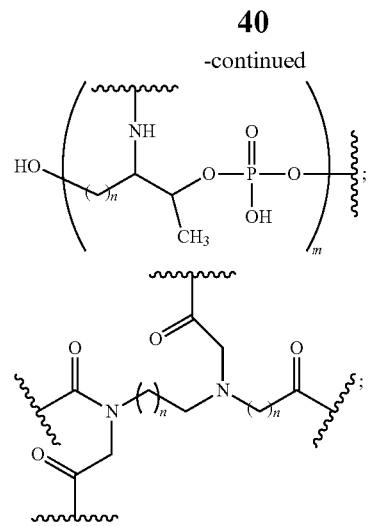
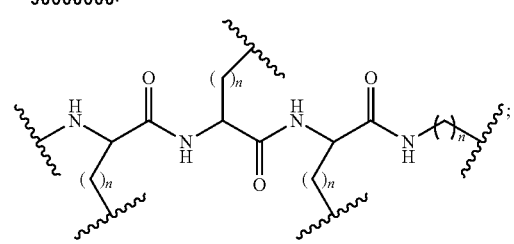
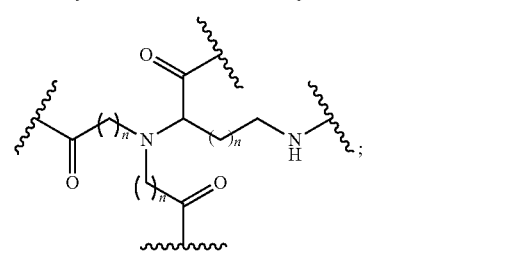
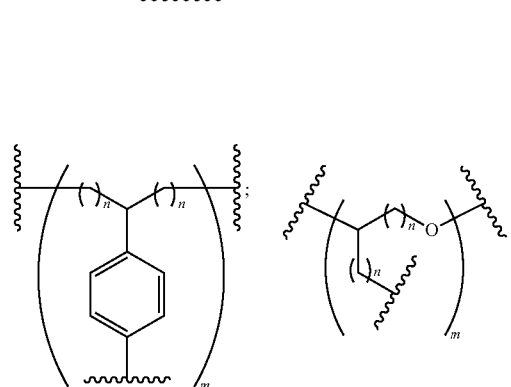
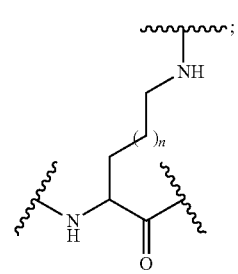

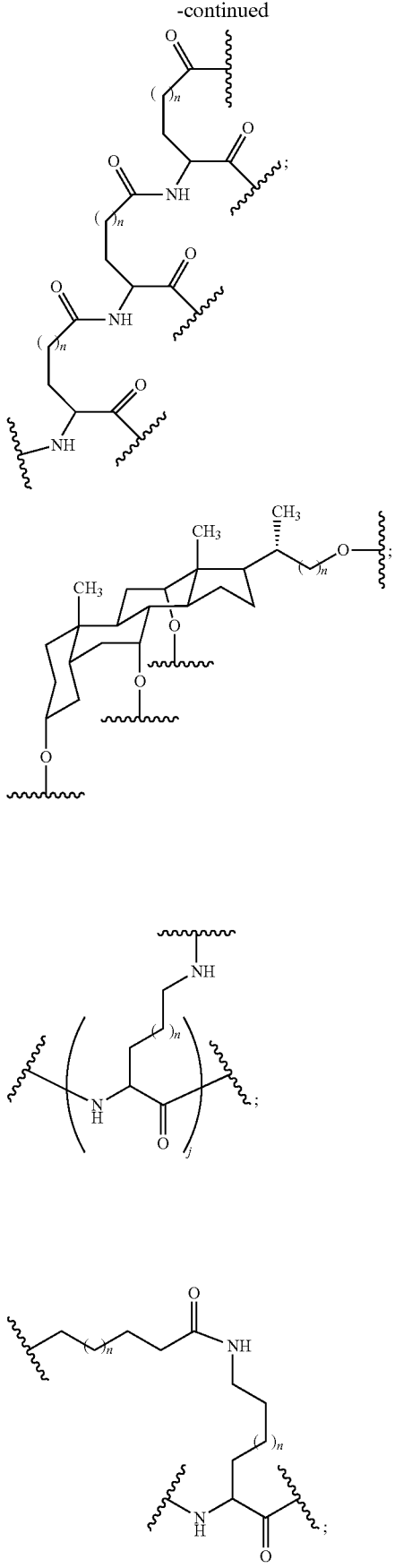
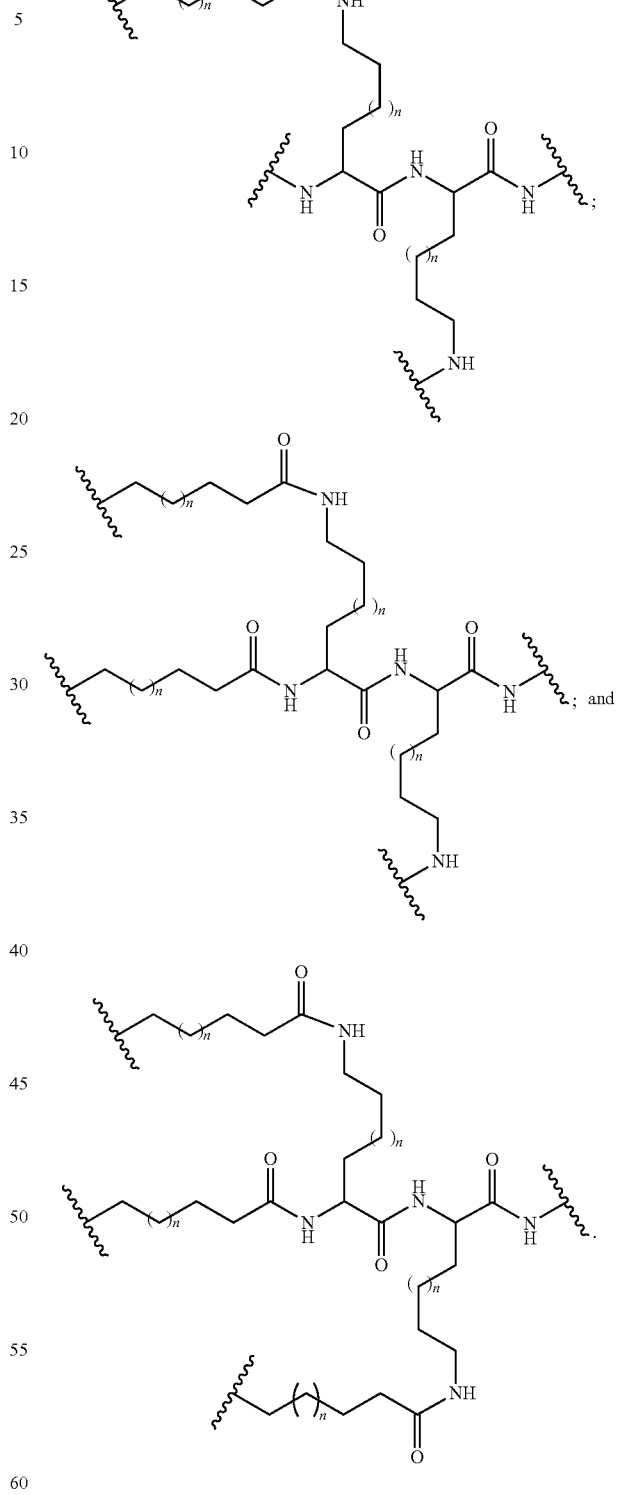
wherein each n is, independently, from 1 to 20;
j is from 1 to 3; and
m is from 2 to 6.
In certain embodiments, a branching group has a structure selected from among:

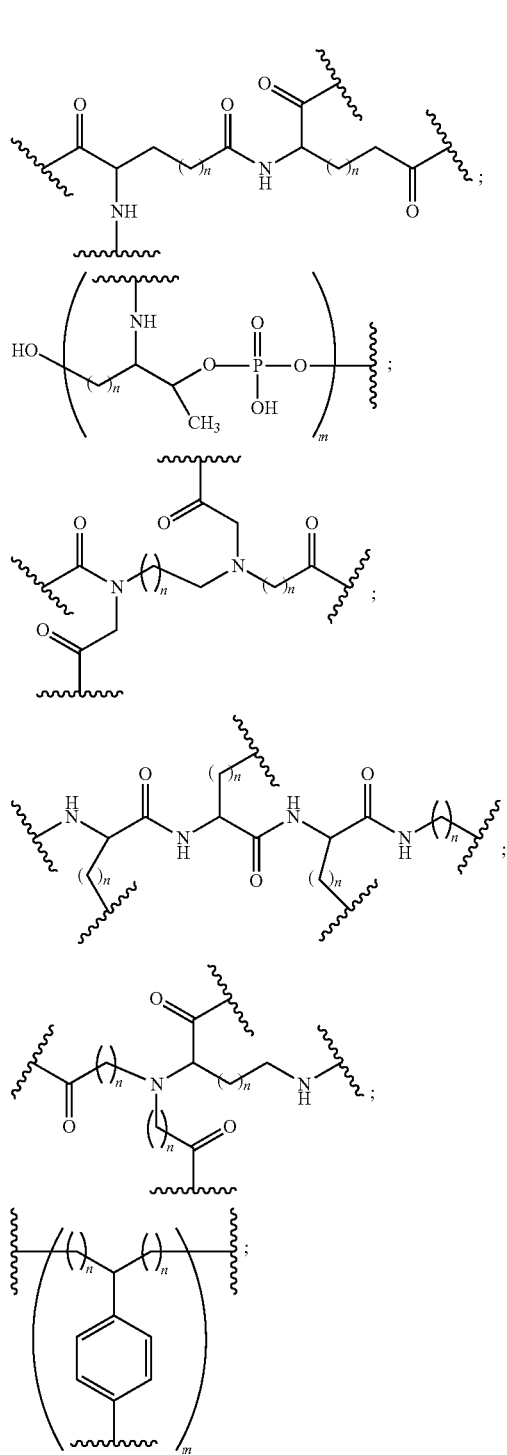
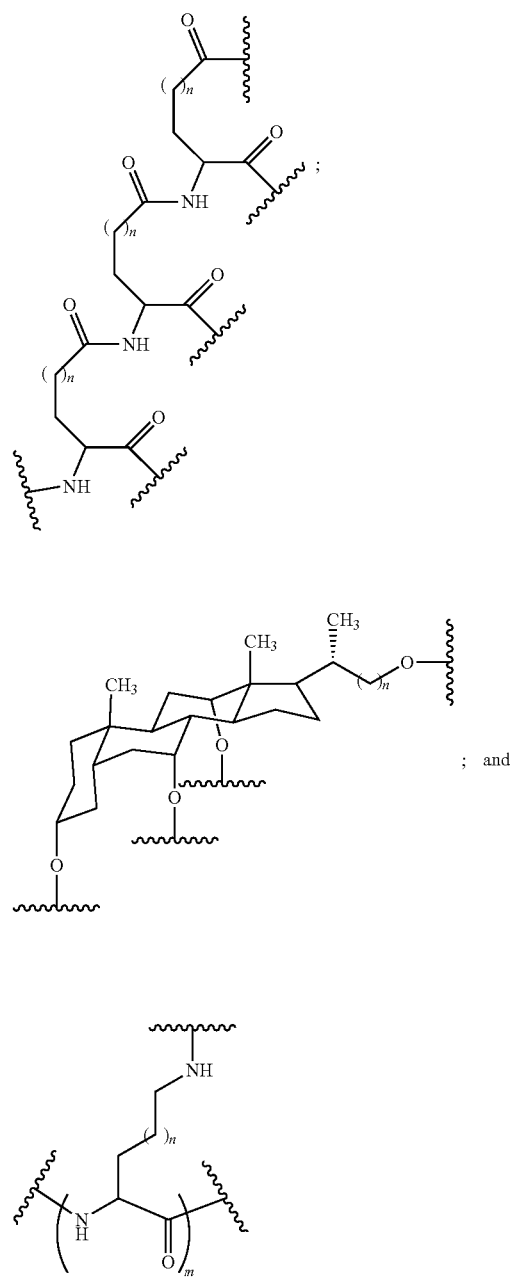
wherein each n is, independently, from 1 to 20; and
m is from 2 to 6.
In certain embodiments, a branching group has a structure selected from among:
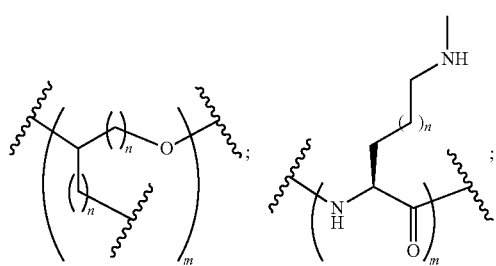
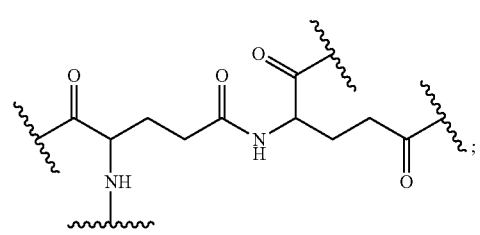

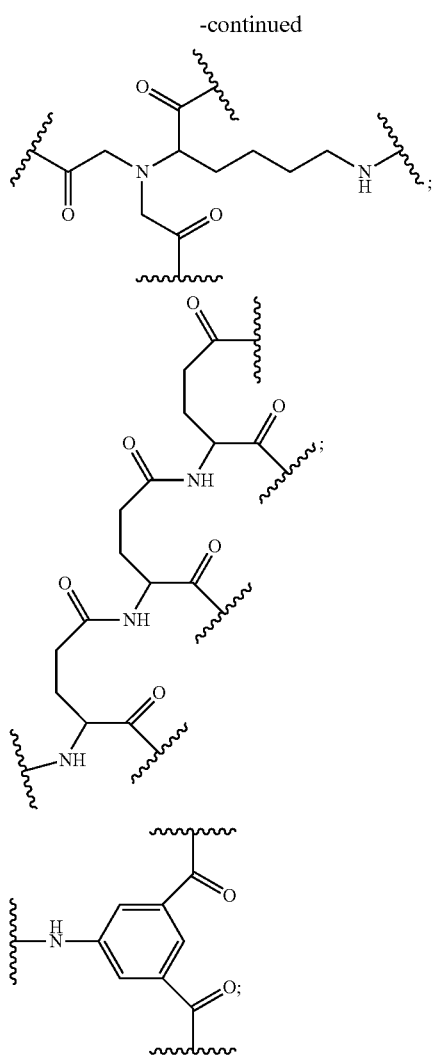
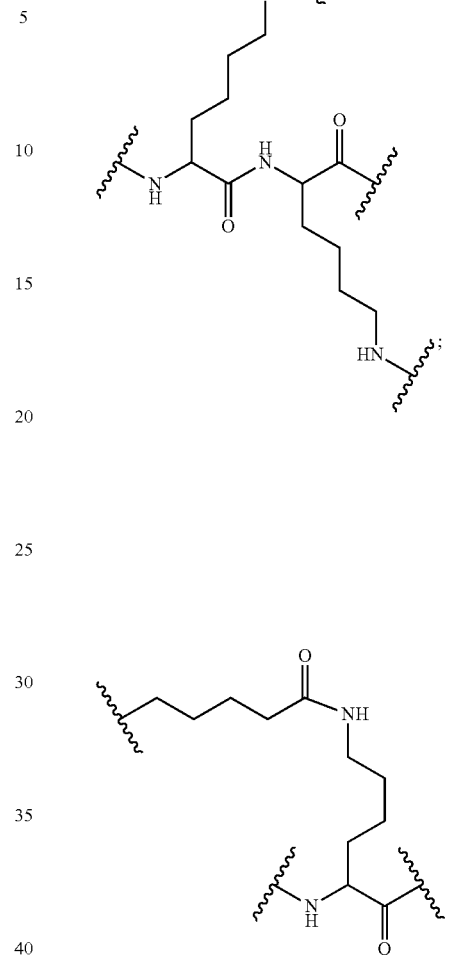
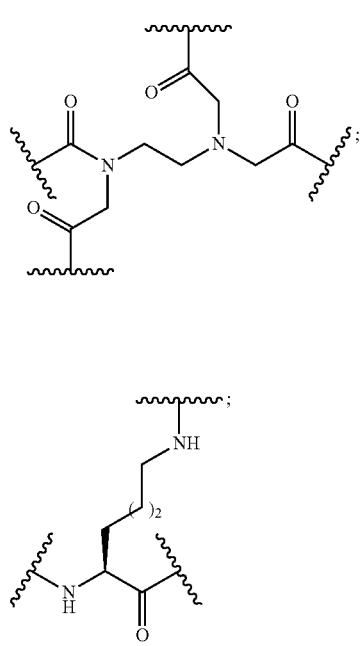
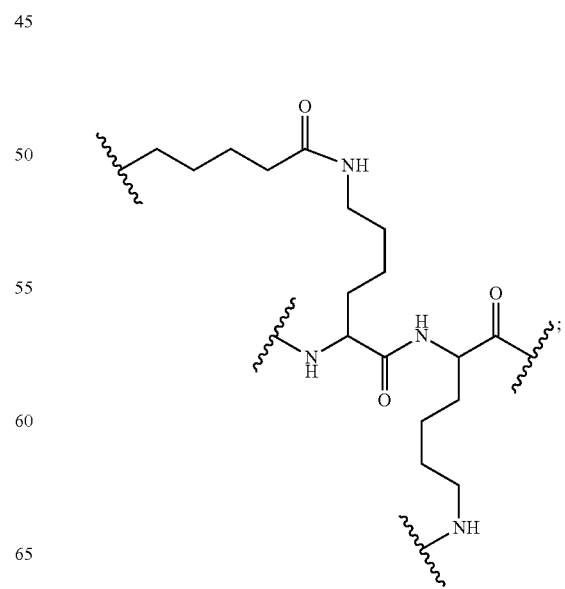

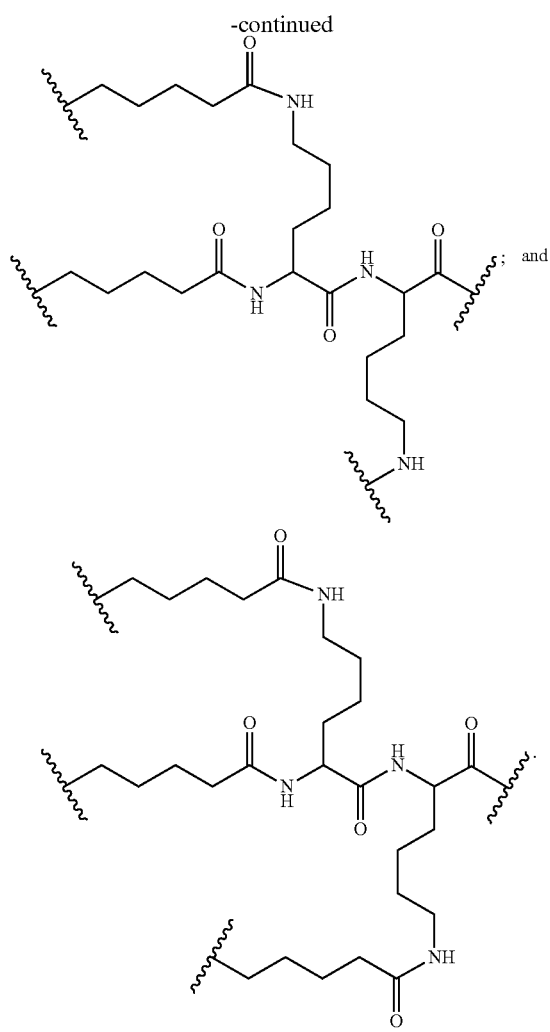
; and

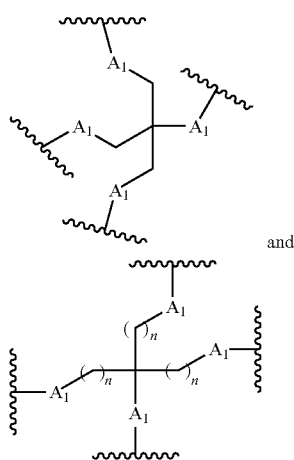

In certain embodiments, a branching group has a structure selected from among:

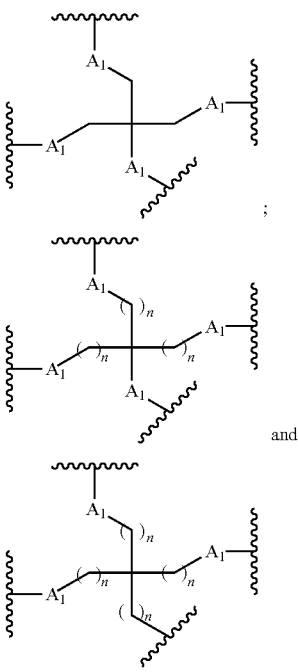

and wherein each $A_1$ is independently, O, S, C=O or NH; and each n is, independently, from 1 to 20.

In certain embodiments, a branching group has a structure selected from among:

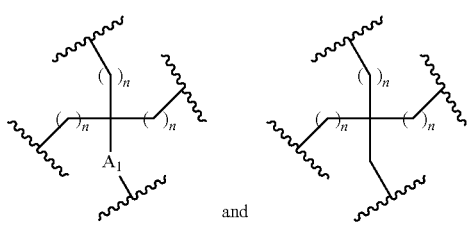

and wherein $A_1$ is O, S, C=O or NH; and
each n is, independently, from 1 to 20.

In certain embodiments, a branching group has the structure:

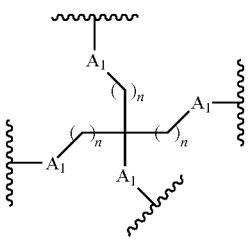

wherein each $A_1$ is, independently, $CH_2$, O or N(H); and
each n is, independently, 1 or 2.

In certain embodiments, a branching group has the structure:

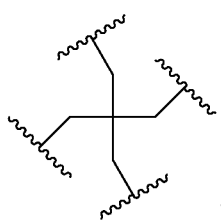

In certain embodiments, a branching group has the structure:

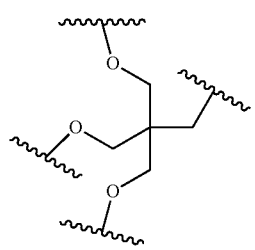

In certain embodiments, a branching group has the structure:

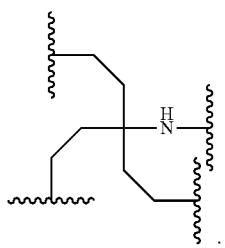 [SMILES: *CCC(CC*)(CC*)N*]

In certain embodiments, a branching group has a structure selected from among:

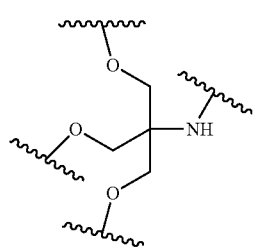

In certain embodiments, reactive conjugate clusters comprise two or more tethers covalently attached to the branching group to the ligands. In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

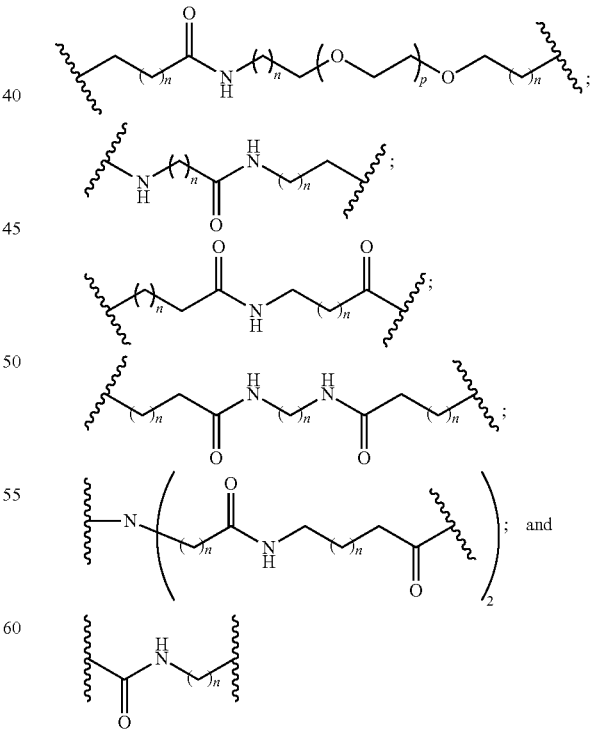

wherein each n is, independently, from 1 to 20; and each p is from 1 to about 6.

In certain embodiments, a tether has a structure selected from among:

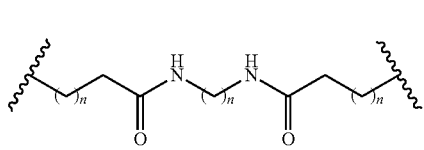

wherein each n is, independently, from 1 to 20.

In certain embodiments, a tether has a structure selected from among:

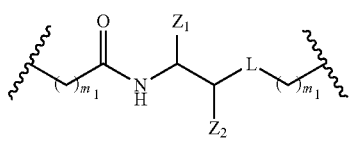

wherein L is either a phosphorus linking group or a neutral linking group;

$Z_1$ is C(=O)O—$R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, a tether has a structure selected from among:

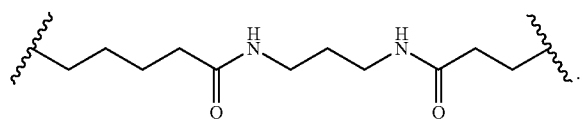 [SMILES: *CCCCC(=O)NCCCNC(=O)CC*]

In certain embodiments, a tether has a structure selected from among:

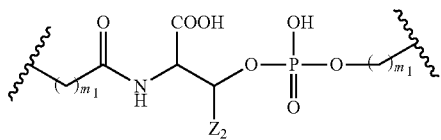

wherein $Z_2$ is H or $CH_3$; and each $m_1$ is, independently, from 0 to 20 wherein at least one $m_1$ is greater than 0 for each tether.

In certain embodiments, a tether has the structure:

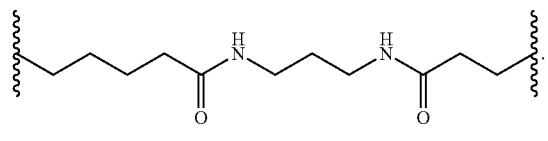 [SMILES: *CCCCC(=O)NCCCNC(=O)CC*]

In certain embodiments, a tether has the structure:

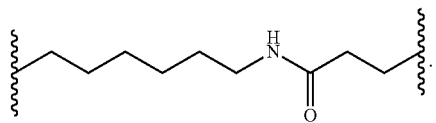 [SMILES: *CCCCCCNC(=O)CC*]

In certain embodiments, a tether comprises a phosphorus linking group. In certain embodiments, a tether does not comprise any amide bonds. In certain embodiments, a tether comprises a phosphorus linking group and does not comprise any amide bonds.

In certain embodiments, the present disclosure provides ligands wherein each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 2 to 6 ligands. In certain embodiments, the reactive conjugate cluster comprises 3 ligands. In certain embodiments, the reactive conjugate cluster comprises 3 N-acetyl galactoseamine ligands. In certain embodiments, the reactive conjugate cluster comprises 3 N-acetyl galactoseamine ligands wherein each of the three hydroxyl groups is acetylated.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments one or more ligand has a structure selected from among:

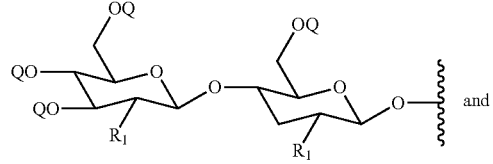 and

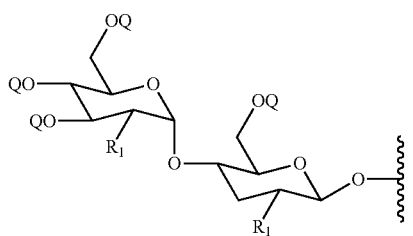

wherein each Q is a protecting group and each R₁ is selected from OQ and NHCOOH.

In certain embodiments one or more ligand has a structure selected from among:

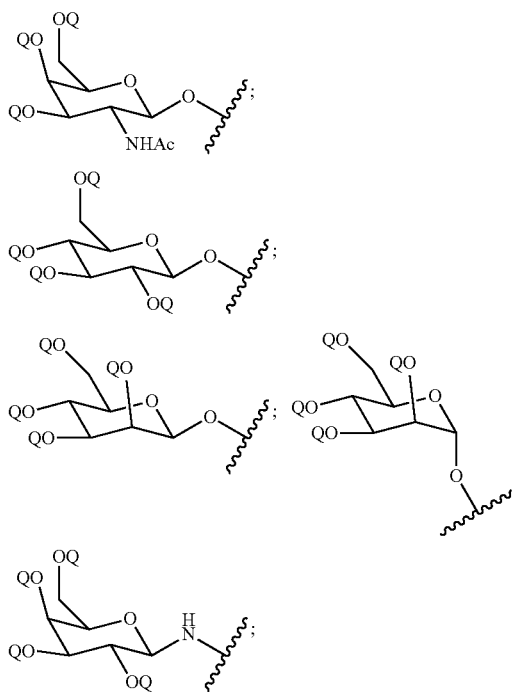

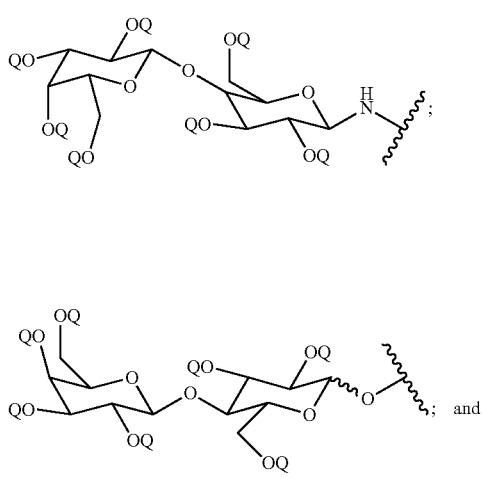

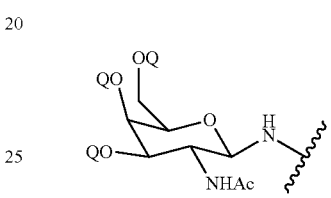

wherein each Q is a protecting group.

In certain embodiments one or more ligand has a structure selected from among:

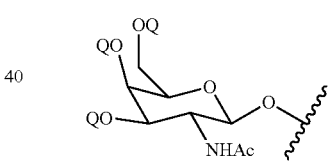

wherein each Q is a protecting group.

In certain embodiments one or more ligand has a structure selected from among:

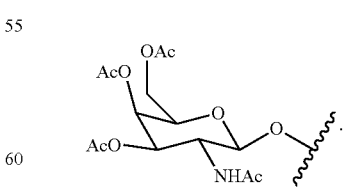

wherein each Q is a protecting group.

In certain embodiments one or more ligand has a structure selected from among:

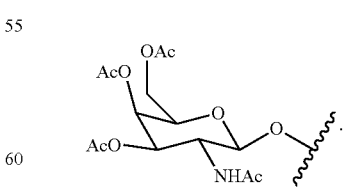

In certain embodiments, reactive conjugate clusters as prepared herein comprise the following structure:

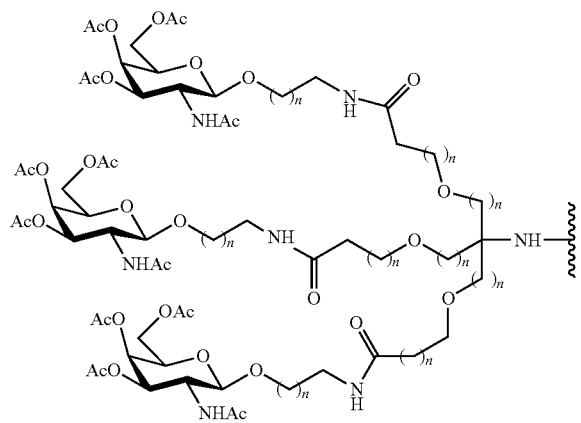

wherein each n is, independently, from 1 to 20.

In certain embodiments, reactive conjugate clusters as prepared herein comprise the following structure:

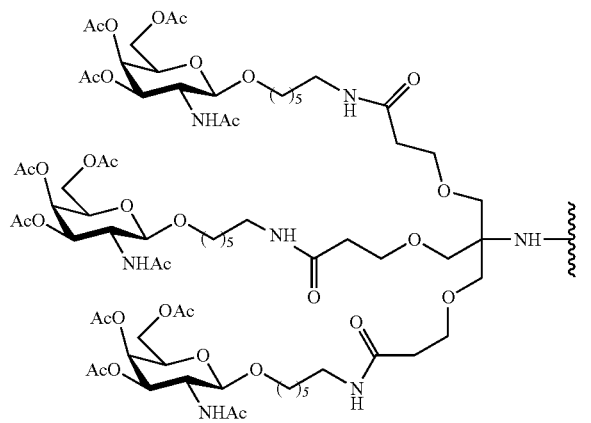

In certain embodiments, reactive conjugate clusters as prepared herein comprise the following structure:

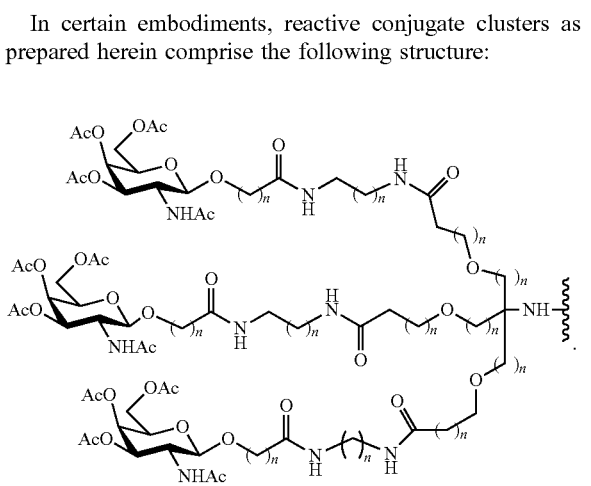

wherein each n is, independently, from 1 to 20.

In certain embodiments, reactive conjugate clusters as prepared herein comprise the following structure:

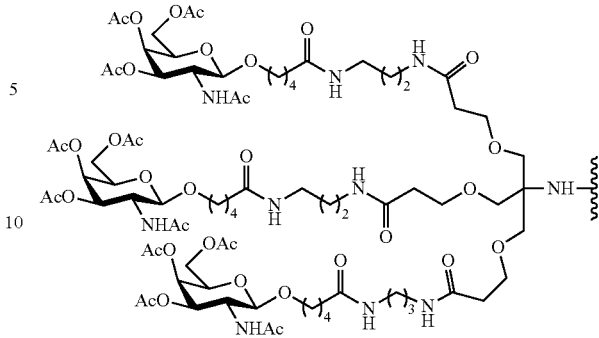

In certain embodiments, reactive conjugate clusters as prepared herein comprise the following structure:

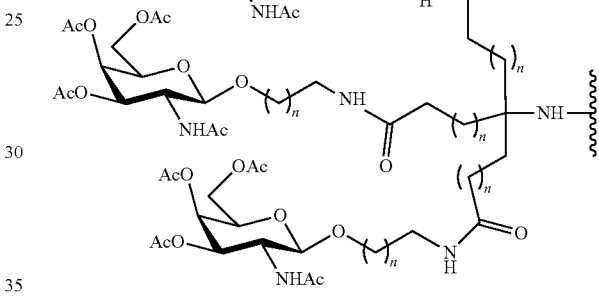

wherein each n is, independently, from 1 to 20.

In certain embodiments, reactive conjugate clusters as prepared herein comprise the following structure:

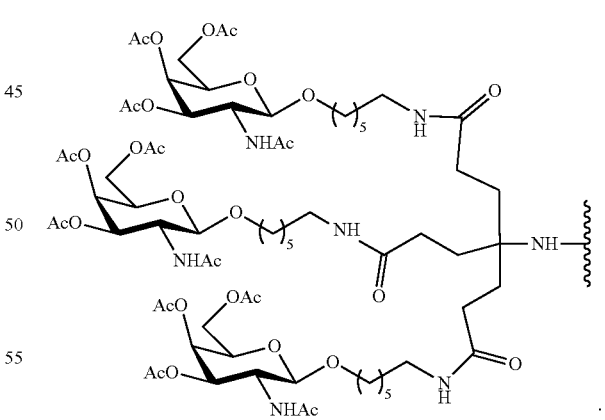

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/

0148740, US 2011/0123520, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, oligomeric compounds prepared as per the methods of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, oligomeric compounds prepared as per the methods of the present invention are RNAi compounds. In certain embodiments, oligomeric oligonucleotides comprising conjugates described herein are ssRNA compounds. In certain embodiments, oligomeric compounds prepared as per the methods of the present invention are paired with a second oligomeric compound to form an siRNA. In certain such embodiments, the second oligomeric compound also comprises a conjugate. In certain embodiments, the second oligomeric compound is any modified or unmodified nucleic acid. In certain embodiments, the oligomeric compounds prepared as per the methods of the present invention are the antisense strand in an siRNA compound. In certain embodiments, the oligomeric compounds prepared as per the methods of the present invention are the sense strand in an siRNA compound.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethylene, pyrimidinylethylene, napthyridinylpropylene and the like. Heteroarylalkyl groups as used herein may optionally include further substituent groups on one or both of the heteroaryl or alkyl portions.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more additional heteroatoms selected from N and S and can be further mono or poly substituted with one or more substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein the terms "halo" and "halogen," refer to an atom selected from fluorine, chlorine, bromine and iodine.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The terms "substituent" and "substituent group," as used herein, are meant to include groups that are typically added to a parent compounds or to further substituted substituent groups to enhance one or more desired properties or provide other desired effects. Substituent groups can be protected or unprotected and can be added to one available site or many available sites on a parent compound. As an example if a benzene is substituted with a substituted alky it will not have any overlap with a benzene that is substituted with substituted hydroxyl. In such an example the alkyl portion of the substituted alkyl is covalently linked by one of its carbon atoms to one of the benzene carbon atoms. If the alky is $C_1$ and it is substituted with a hydroxyl substituent group (substituted alkyl) then the resultant compound is benzyl alcohol ($C_6H_5CH_2OH$). If the benzene were substituted with a substituted hydroxyl group and the hydroxyl was substituted with a $C_1$ alkyl group then the resultant compound would be anisole ($C_6H_5OCH_3$).

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein the term "nucleobase" generally refers to the nucleobase of a nucleoside or modified nucleoside. The term "heterocyclic base moiety" is broader than the term nucleobase in that it includes any heterocyclic base that can be attached to a sugar or sugar surrogate group to prepare a nucleoside or modified nucleoside. In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines). In certain embodiments, each heterocyclic base moiety is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine. In certain embodiments, each heterocyclic base moiety is, independently, uracil, thymine, cytosine, 5-methylcytosine, adenine, 6-N-benzoyladenine or guanine.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

As used herein the term "sugar moiety" refers to naturally occurring sugars having a furanose ring system (ribose and 2'-deoxyribose), synthetic and/or non-naturally occurring sugars having a modified furanose ring system and sugar surrogates wherein the furanose ring has been replaced with a mono or polycyclic ring system such as for example a morpholino or hexitol ring system or a non-cyclic sugar surrogate such as that used in peptide nucleic acids. The sugar moiety of a monomer subunit provides the reactive groups that enable the linking of adjacent monomer subunits into an oligomeric compound. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH($CH_3$)-4', 2'-O—$CH_2$-4' or 2'-O—

(CH$_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system such as that used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

As used herein the term "sugar substituent group" refers to a group that is covalently attached to a sugar moiety. In certain embodiments, examples of sugar sub stituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are C$_1$ to C$_6$. In certain embodiments, the alkenyl and alkynyl groups are C$_2$ to C$_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-OCH$_3$, 2'-O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_2$O]$_m$CH$_3$, 2'-O(CH$_2$)$_2$SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$]$_2$, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each R$_p$, R$_q$ and R$_r$ is, independently, H, substituted or unsubstituted C$_1$-C$_{10}$ alkyl or a protecting group and where n and m are from 1 to about 10.

As used herein the term "monomer subunit" is meant to include all manner of monomers that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribnucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates.

As used herein, the term "nucleoside" refers to a nucleobase-sugar combination. The two most common classes of such nucleobases are purines and pyrimidines. The term nucleoside includes β-D-ribonucleosides and β-D-2'-deoxyribonucleosides.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose ring system or a modified furanose ring system. Modified furanose ring systems include 4'-S analogs, one or more substitutions at any position such as for example the 2', 3', 4' and 5' positions and addition of bridges for form additional rings such as a 2'-O—CH(CH$_3$)-4' bridge. Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons atoms. In certain embodiments, bicyclic nucleosides have a bridge between the 4' and 2' carbon atoms. Examples of such 4' to 2' bridged bicyclic nucleosides, include but are not limited to one of formulae: 4'-($CH_2$)—O-2' (LNA); 4'-($CH_2$)—S-2'; 4'-($CH_2$)$_2$—O-2' (ENA); 4'-CH($CH_3$)—O-2' and 4'-C—H($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4'-$CH_2$—N(OCH_3)-2' (and analogs thereof see published International Application WO2008/150729, published Dec. 11, 2008); 4'-$CH_2$—O—N($CH_3$)-2' (see U.S. Pat. No. 7,96,345, issued on Apr. 13, 2010,); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya, et al., J. Org. Chem., 2009, 74, 118-134); and 4'-$CH_2$—$CH_2$-2' and 4'-$CH_2$—C—(=$CH_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A., 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,741,457; 7,696,345; 7,547,684; 7,399,845; 7,053,207; 7,034,133; 6,794,499; 6,770,748; 6,670,461; 6,525,191; 6,268,490; U.S. Patent Publication Nos. US2008-0039618; U.S. Patent Application Ser. Nos. 61/099,844; 61/097,787; 61/086,231; 61/056,564; 61/026,998; 61/026,995; 60/989,574; International applications WO2009/006478; WO2008/154401; WO2008/150729; WO 2007/134181; WO 2005/021570; WO 2004/106356; WO 94/14226). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

As used herein, the term "oligomeric compound" refers to a contiguous sequence of linked monomer subunits. Each linked monomer subunit normally includes a heterocyclic base moiety but monomer subunits also include those without a heterocyclic base moiety such as abasic monomer subunits. In certain embodiments, at least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present. In certain embodiments, each internucleoside linkage is, independently, a phosphorothioate or a phosphodiester internucleoside linkage. In certain embodiments, essentially each internucleoside linkage is a phosphodiester internucleoside linkage. In certain embodiments, essentially each internucleoside linkage is, a phosphorothioate internucleoside linkage.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are nonionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5), amide-4 (3'-$CH_2$—N(H)—C(=O)-5'), formacetal (3'—O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary" "in reference to nucleobases refers to a pair of nucleobases that do not form hydrogen bonds with one another or otherwise support hybridization.

As used herein, "hybridization" refers to the pairing of complementary oligomeric compounds (e.g., an antisense compound and its target nucleic acid). While not wanting to be limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, Methods, 2001, 23, 206-217; Gait et al., Applications of Chemically synthesized RNA in RNA: Protein Interactions, Smith, Ed., 1998, 1-36; Gallo et al., Tetrahedron, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In certain embodiments, methods of synthesizing of oligomeric compounds are provided that utilize support medium. In certain embodiments, reactive groups on the support medium are first functionalized with Unylinker™ linking groups prior to addition of the first monomer subunit. A first monomer subunit is attached to a support medium with subsequent monomer subunits iteratively coupled to provide a desired oligomeric compound. The industry standard for large scale oligomeric compound synthesis uses solid support media in a reaction vessel. The growing oligomeric compound is reacted and washed with various reagents and solvents while attached to the solid support. In certain embodiments, support media can be selected having variable solubility in different solvents to allow the growing support bound oligomeric compound to be either in or out of solution at various points in the synthesis process as desired. In certain embodiments, soluble supports include soluble polymer supports that allow precipitating and dissolving the iteratively synthesized product at desired points in the synthesis (Gravert et al., Chem. Rev., 1997, 97, 489-510).

All documents, or portions of documents, cited in this application, including, but not limited to, patents, patent applications, articles, books, and treatises, are hereby expressly incorporated by reference in their entirety for any purpose.

Those skilled in the art, having possession of the present disclosure will be able to prepare oligomeric compounds, comprising a contiguous sequence of linked monomer subunits, of essentially any viable length. While in certain embodiments, oligomeric compounds provided herein can be prepared as described, the following examples serve only to illustrate and are not intended to be limiting.

Example 1

Preparation of Compound 2

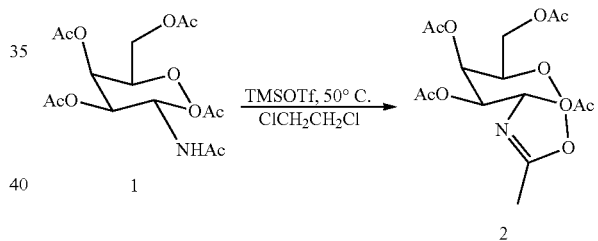

Compound 1 (2-acetamido-1,3,4,6-tetra-O-acetyl-2-deoxy-β-D-galactopyranose or galactosamine pentaacetate) is commercially available. Following a published procedure, Compound 2 was obtained in a 93% yield (Rensen et al., J. Med. Chem., 2004, 47, 5798-5808; Nakabayashi et al., Carbohyrate Res., 1986, 150, C7).

Example 2

Preparation of Compound 5

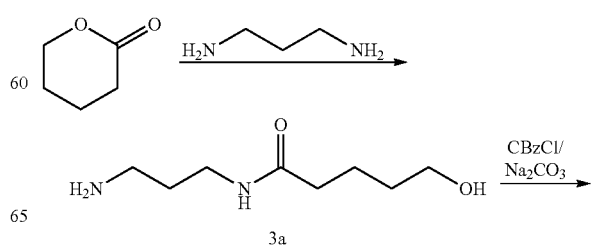

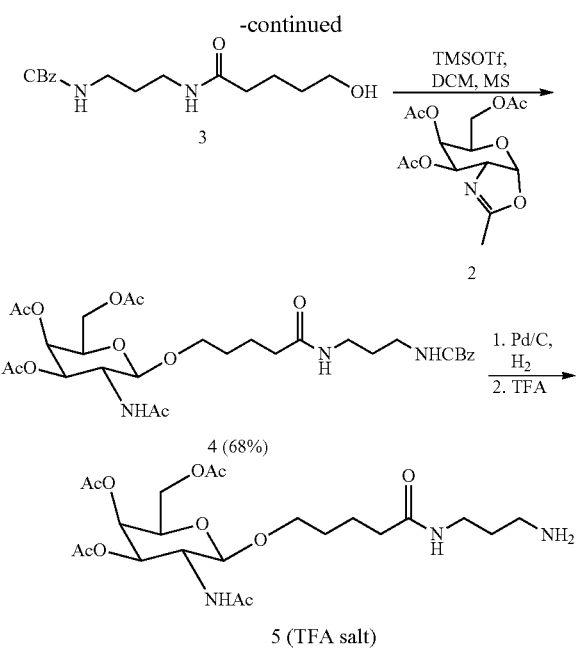

Delta-valerolactone (46.3 mL, 499.4 mmol, commercially available) was added to 1,3-diaminopropane (148 mL, 1773 mmol, commercially available) in a round bottom flask. The reaction was vigorously stirred. The clear solution obtained was stirred at room temperature for 12 hours and monitored by LCMS. The reaction mixture was concentrated under reduced pressure to provide the crude intermediate Compound 3a (94 g) which was used for the next step without purification. The structure of the crude amide intermediate compound (Compound 3a) was confirmed by LCMS and $^1$H NMR.

The crude amide intermediate compound (Compound 3a) from above (94 g, 499.42 mmol) and sodium carbonate (80 g, 749.1 mmol) were suspended in a mixture of 1,4-dioxane (900 mL) and water (180 mL) and benzyl chloroformate (106 mL, 749.1 mmol) was added. The reaction mixture was stirred at room temperature for 12 hours and then analyzed by LCMS. The reaction was partitioned with ethyl acetate and water. The organic layer was separated and the aqueous layer was extracted with ethyl acetate twice. The ethyl acetate layers were combined and concentrated. The residue was suspended in water (900 mL) and extracted with dichloromethane/5% MeOH (450 mL three times). The dichloromethane layers were combined, dried over sodium sulfate and concentrated to thick white slurry. The crude material was crystallized with acetone/hexanes to provide Compound 3 as white solid (119.64 g, 78% in these two steps). The structure of Compound 3 was confirmed by LCMS and $^1$H NMR.

Compound 2 (17.2 g, 52.2 mmol), Compound 3 (16.11 g, 52.2 mmol) and pre-dried molecular sieves (20 g) were suspended in dry dichloromethane (120 mL). The mixture was stirred at room temperature for 30 minutes and TMSOTf (4.7 mL) was added. The reaction was stirred at room temperature for 12 hours and then analyzed by LCMS. The reaction mixture was poured into icy NaHCO$_3$ and extracted with dichloromethane. The dichloromethane extract was washed with brine and concentrated to dryness. The crude product was purified via Biotage silica gel column that was eluted with 2%, (5 column volumes "CV"), 3% (3 CV), 5% (4 CV) and 8% (3 CV) MeOH in dichloromethane to provide Compound 4 as a white foam (22.8 g, 68%). The structure of Compound 4 was confirmed by LCMS and $^1$H NMR.

Compound 4 (5.6 g) was dissolved in ethyl acetate (40 mL) and methanol (40 mL) and palladium on carbon (0.93 g, wet) was added. The reaction was stirred under hydrogen at room temperature for 12 hours and then analyzed by LCMS. The reaction was filtered through a celite pad. The celite pad was thoroughly washed with a mixture of ethyl acetate and methanol (50 mL each). The wash filtrate and filtered residue were combined, TFA (0.67 mL) was added, then the solvent was removed under reduced pressure. The residue was co-evaporated with toluene (2×30 mL) to dryness to provide Compound 5 (TFA salt) as a yellow foam (5.42 g, quantitative). The structure of Compound 5 was confirmed by LCMS.

Example 3

Preparation of Compound 7

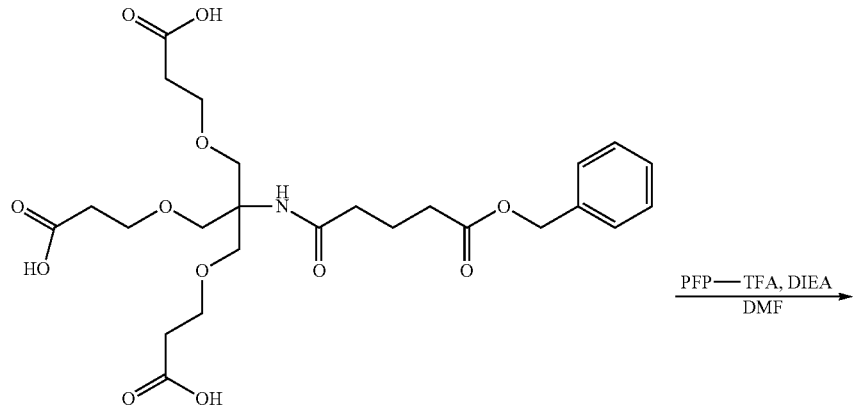

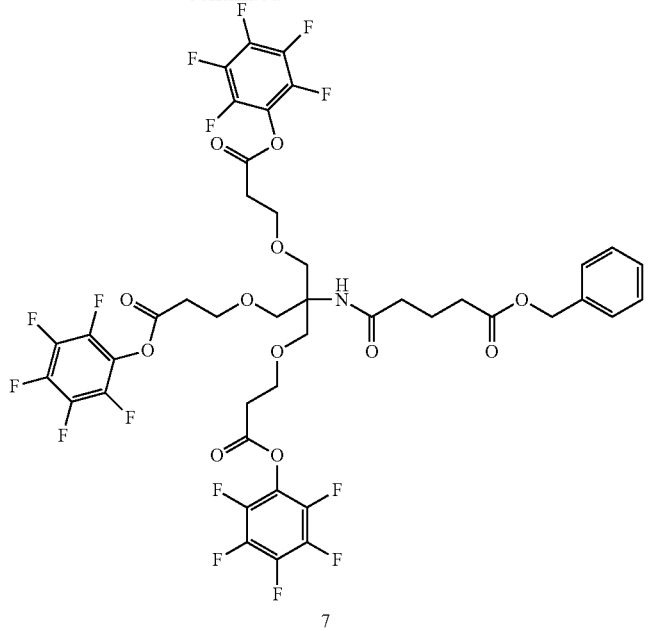

7

Compound 6 (20 g, commercially available) was dissolved in DMF (150 mL) and DIEA (51 mL) was added. To this mixture, pentafluorophenyl trifluoroacetate (25.4 mL, PFP-TFA) was slowly introduced. The color of the reaction went from colorless to burgundy. The reaction was stirred at RT overnight and monitored by LCMS. The reaction was treated with 1 N NaHSO$_4$ (500 mL) and extracted with ethyl acetate (600 mL). The ethyl acetate extract was washed with brine (150 mL×2), sat. NaHCO$_3$ (200 mL×2), brine (150 mL×2) and dried over Na$_2$SO$_4$. The ethyl acetate was concentrated to dryness and purified via Biotage (340 g) silica gel column eluted with 10% (3 CV), 20% (3 CV), 30% (6 CV) ethyl acetate in Hexanes to provide Compound 7 as an orange oil (31.87 g, 83%). The structure of Compound 7 was confirmed by LCMS and $^1$H NMR.

Alternate Method for the Preparation of Compound 7

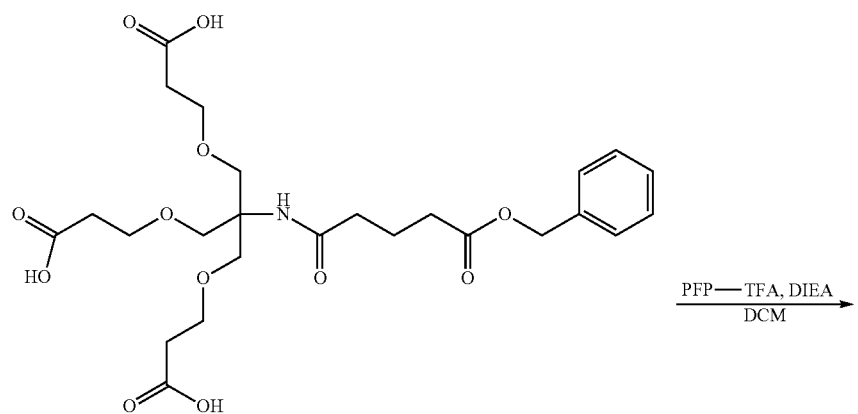

6

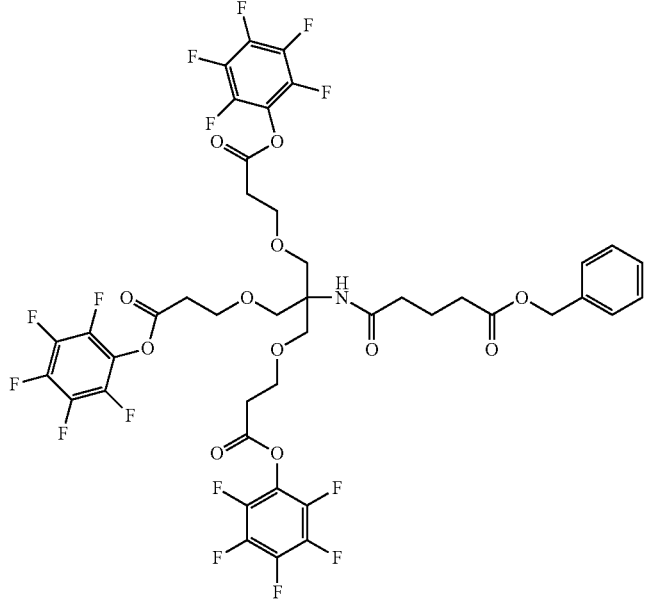

7

Compound 6 (commercially available from TCI Scientific, Edmonton, AB, Canada, product # TCS083008) was initially recrystallized as the purity was assayed to be only at about 70%. Purification of Compound 6 provided much purer Compound 7. Note: recrystallization is not required for lots already at about 95% purity. Compound 6 (148.56 grams) was suspended in dry ACN (625 mL) with stirring and heating to 40° C. until all solids dissolved. The reaction was allowed to cool to room temp slowly and then cooled in a refrigerator at 4° C. for one hour. Over the next 30 minutes, a white solid precipitated. The resulting slurry was diluted with cold ACN (250 mL), and was chilled in a salted ice bath (−2° C.) for 1 hour. The mixture was filtered and the solid filtrate rinsed with cold ACN (200 mL) and cold methyl tertiary butyl ether (MTBE, 400 mL) to provide Compound 6 (102 grams, 69% recovery, at 97% purity).

Purified Compound 6 (50 g, 91 mmol) was suspended in dry DCM (425 mL). The reaction mixture was cooled in an ice bath and diisopropylethylamine (DIEA) was added (120 mL, 730 mmol, 8 eq.), and the reaction was purged with nitrogen. PFP-TFA (53.5 mL, 311 mmol, 3.4 eq.) was added slowly to the reaction mixture via addition funnel (~3.5 mL/min). The color of the reaction changed from colorless to light pink and gave off a light smoke which was blown away with a stream of nitrogen. After the addition was complete, the reaction was stirred on ice for 15 minutes, then at room temperature for 1 hour. Over the course of the reaction the color changed to burgundy and then to dark orange. The reaction was monitored by TLC (7:3 hexanes/EtOAc) and LCMS.

At completion ice water (400 mL) and saturated aqueous $NaHCO_3$ (100 mL) was added. The reaction mixture was stirred vigorously, and was transferred to a separatory funnel. The organic layer was recovered and washed with water (2×500 mL), then with brine (1×500 mL). The organics were dried over $MgSO_4$, filtered, and concentrated under reduced pressure to a dark orange oil to provide the crude product (72.0 g). The crude product was diluted with DCM (~100 mL), and was passed through a pad of silica gel (600 mL fritted funnel, 4" wide, 2.5" thick). The product was eluted with DCM (~500 mL). The majority of the orange color was trapped by the silica gel. The filtrate was concentrated under reduced pressure to give Compound 7 (89 g, 93%) as a dark orange syrup. The structure of Compound 7 was confirmed by LCMS, $^1$H NMR and $^{19}$F NMR.

Example 4

Preparation of Compound 8a

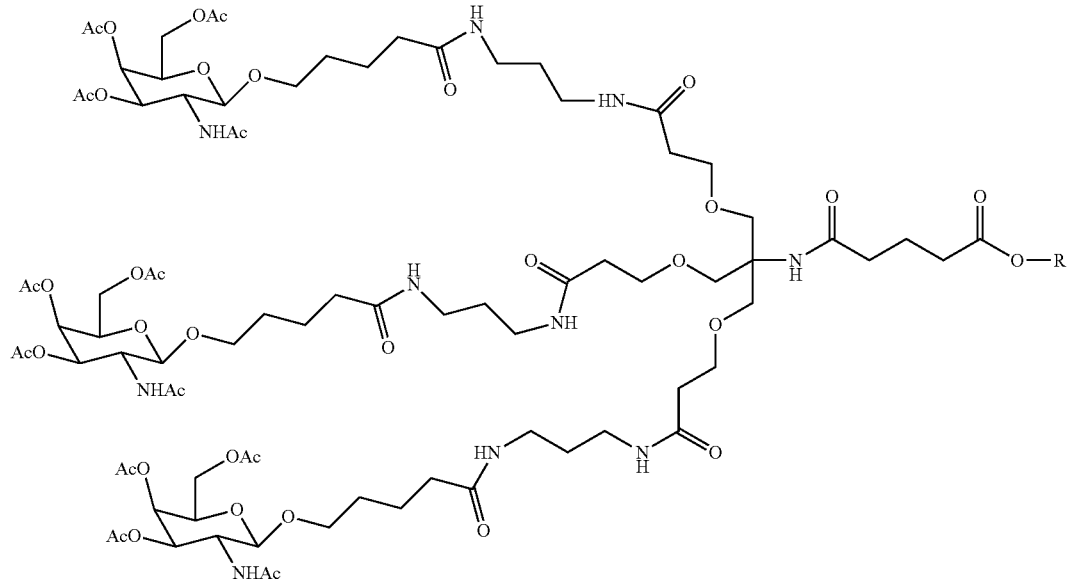

Compound 8a, R = benzyl

Compound 5 (5.35 g, TFA salt) and Compound 7 (2.5 g) were dissolved in acetonitrile (20 mL) and DIEA (2.5 mL) was added (color changed from yellow to light brown). The reaction mixture was stirred at room temperature and monitored by LCMS (reaction was done in 20 minutes). The reaction mixture was diluted with dichloromethane (200 mL) and washed with 10% aqueous ammonium chloride solution (100 mL), brine (100 mL), and dried over $Na_2SO_4$. The organic phase was concentrated under reduced pressure to yield crude product (5.58 g, 90%) as light yellow foam. Compound 8a was confirmed by LCMS and $^1H$ NMR.

Example 5

Preparation of Compound 8c

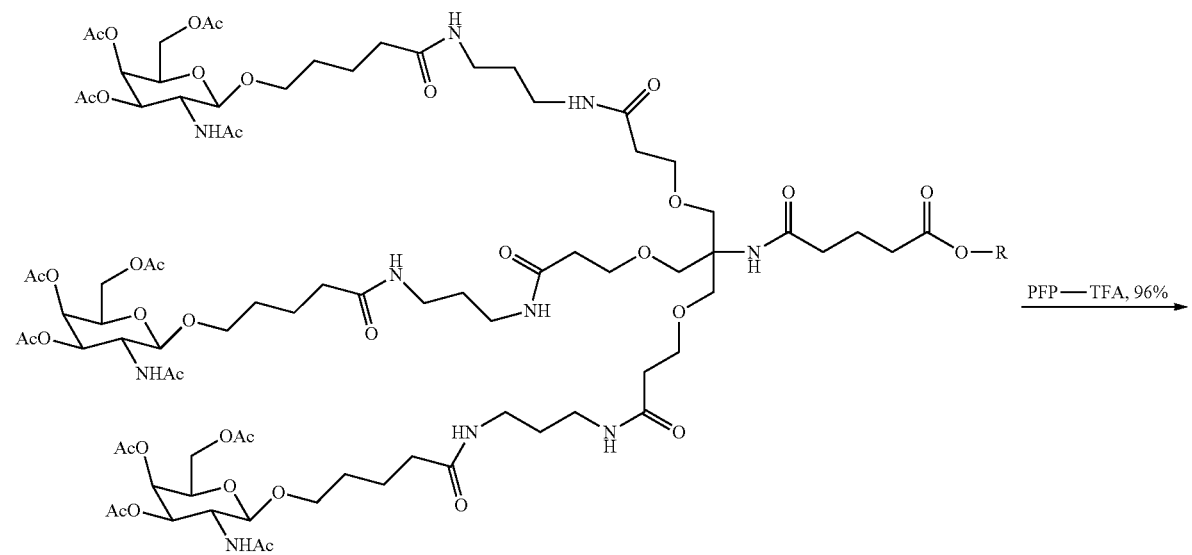

Compound 8b, R = H

Compound 8c, R = pentafluorophenyl

Compound 4 (10.24 g, 16.1 mmol) and Compound 7 (5 g, 4.2 mmol) were dissolved in acetonitrile (100 mL). To this mixture, Pd(OH)$_2$/C (20 wt %, 3.0 g) was added. The reaction mixture was flushed with hydrogen gas and stirred under hydrogen atmosphere at room temperature. The progress of the reaction was monitored by LCMS and the reaction was completed after three hours. The reaction mixture was filtered through a pad of celite. The celite pad was washed thoroughly with acetonitrile. The wash filtrate and residue were combined and concentrated under reduced pressure. The residue was purified by silica gel column chromatography and eluted with 5-30% methanol in dichloromethane to yield 8b (7.43 g, 81%) The structure of Compound 8b was confirmed by LCMS and $^1$H NMR.

Compound 8b (5.2 g) and TEA (1.14 mL, 3 eq.) were dissolved in DMF (25 mL). To this PFP-TFA (0.937 mL, 2 eq.) was added (color changed from yellow to burgundy) dropwise. The reaction was completed after one hour as determined by LC MS analysis. The DMF was removed under reduced pressure at 50° C. The residue was diluted with dichloromethane and the organic phase was washed with 1N NaHSO$_4$ (80 mL), saturated aqueous sodium bicarbonate solution and brine. The organic phase was dried over Na$_2$SO$_4$, filtered and evaporated to yield 8c (5.71 g, quantitative) as a light pink foam. The structure of Compound 8c was confirmed by LCMS, $^1$H NMR and $^{19}$F NMR.

Example 6

Preparation of Compound 12

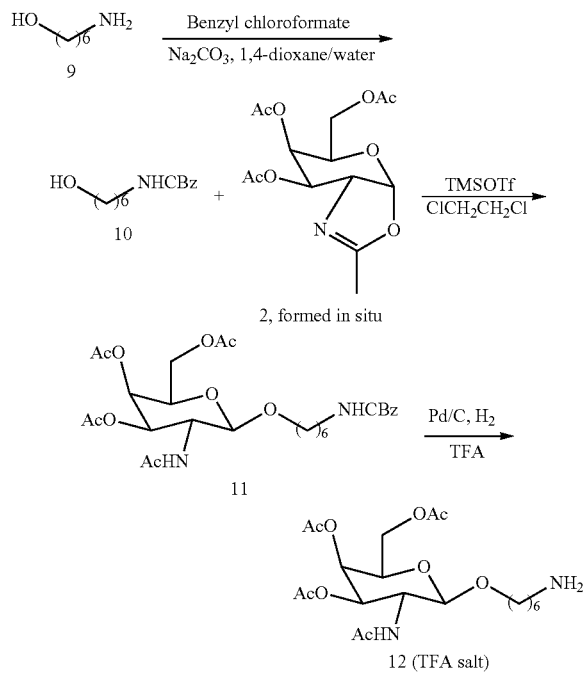

Aminohexanol (Compound 9, 70 g, 0.597 mol, commercially available) and Na$_2$CO$_3$ (110.79 g, 1.059 mol, 1.75 eq.) were added to a mixture of 1,4-dioxane (1400 mL) and water (300 mL) in a 3.0 L bottom flask equipped with mechanical stirrer and stirred for 1 hour to dissolve the salt. The resulting clear solution was cooled in an ice bath and benzyl chloroformate (178.32 g, 1.045 mol, 1.75 eq.) was added dropwise by addition funnel. The mixture was stirred overnight and allowed to warm slowly to room temperature resulting in the formation of a white precipitate. The precipitate was filtered and washed with ethyl acetate and the filtrate was extracted with ethyl acetate. The combined organic phases were washed with saturated NaHCO$_3$ (500 mL), brine (500 mL), dried over Na$_2$SO$_4$, filtered and the filtrate was evaporated under reduced pressure to provide a white solid. The white solid was suspended in hexanes, filtered and rinsed with fresh hexanes to provide purified Compound 10 (129.0 g, 86%). The structure of Compound 10 was confirmed by LCMS and $^1$H NMR.

Compounds 1 and 10 were dried over P$_2$O$_5$ overnight under high vacuum at 35° C. in separate flasks. Compound 1 (150 g, 0.385 mol) was dissolved in anhydrous dichloroethane (500.0 mL) with stirring under nitrogen at room temperature. To the resulting clear solution was added TMSOTf (119.87 g, 0.539 mol, 1.5 eq.) with stirring for two hours to form Compound 2 in Solution 1.

Compound 10 (106.51 g, 0.424 mol, 1.1 eq.) was dissolved in anhydrous dichloroethane (1.0 L) and molecular sieves were added (powder molecular sieves ~30 g, dried at 275° C. overnight and subsequently cooled to room temperature under high vacuum) with stirring maintained for 40 minutes. To the resulting mixture was added Solution 1 by cannula dropwise slowly over a period of 1 hour with stirring for an additional 2 hours. The reaction mixture was filtered and the filtrate dripped onto an ice cold saturated solution of NaHCO$_3$ (300 mL). The organic phase was separated and washed with DI water (500 mL), brine (500 mL), dried over Na$_2$SO$_4$, filtered and evaporated to dryness to provide the crude material as a white solid. The crude material was suspended in EtOAc/hexanes (800 mL) and filtered to provide pure white crystalline product, Compound 11 (111.44 g). The filtrate was concentrated and the residue purified by silica gel chromatography eluted with DCM/MeOH (97/3) and the collected fractions concentrated and suspended in EtOAc/hexane (400 mL) and filtered to provide additional Compound 11 (44.0 g, for a combined yield of 70%, 155.14 g). The structure of Compound 11 was confirmed by LCMS and $^1$H NMR.

Compound 11 (5.6 g) was dissolved in ethyl acetate (40 mL) and methanol (40 mL) and palladium on carbon (0.93 g, 10 wt % Degussa type wet) was added. The reaction mixture was was stirred under hydrogen at room temperature for 12 hours and then analyzed by LCMS. The reaction was filtered through a celite pad, and the celite pad was thoroughly washed with a mixture of ethyl acetate and methanol (50 mL each). The wash filtrate and filtered residue were combined, TFA (0.74 mL) was added, then the solvent was removed under reduced pressure. The residue was co-evaporated with toluene (2×30 mL) to dryness to provide Compound 12 as a yellow foam (5.42 g, quantitative). The structure of compound 12 was confirmed by LCMS.

Example 7

Preparation of Compound 13c

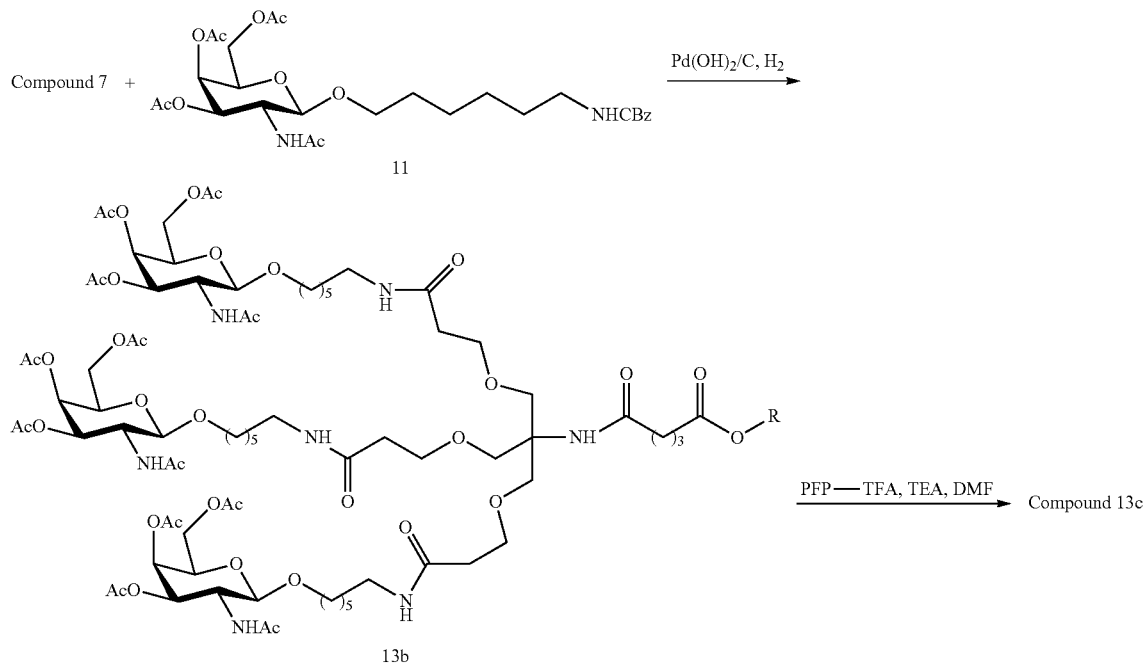

Compound 13b: R = H
Compound 13c: R = pentafluorophenyl

Compound 7 (6 g) and Compound 11 (11.39 g) were dissolved in a mixture of ethyl acetate (70 mL) and MeOH (35 mL). Pd(OH)$_2$/C (2.2 g, 20 wt %) was added and the reaction mixture was stirred at room temperature under H$_2$ with monitoring at 2 hour time points. At 12 hours the reaction was filtered and concentrated to dryness. The resulting crude product was purified via silica gel column eluted with dichloromethane (3CV), ethyl acetate (6CV), dichloromethane (3CV), 5% MeOH (6CV) and 10% MeOH (6CV) in dichloromethane to provide Compound 13b (6.9 g, 69%) as a light yellow foam. The structure of Compound 13b was confirmed by LCMS and $^1$H NMR.

Compound 13b (5.2 g) and TEA (1.14 mL, 3 eq.) were dissolved in DMF (25 mL) and PFP-TFA (0.937 mL, 2 eq.) was added. After one hour, LC MS analysis showed that the reaction was completed. The DMF was removed under reduced pressure at 50° C. The residue was diluted with dichloromethane and the solution thus obtained was washed with 1N NaHSO$_4$ (80 mL), brine, saturated aqueous sodium bicarbonate and brine, dried over Na$_2$SO$_4$, filtered and concentrated to dryness to yield compound 13c (5.75 g, quantitative) as a light pink foam. The structure of Compound 13c was confirmed by LCMS, $^1$H NMR and $^{19}$F NMR.

Alternate Method for the Preparation of Compound 13c

Compound 7 (55 g, 52.9 mmol) and Compound 11 (94 g, 161.9 mmol, 3.06 eq.) were dissolved in dry THF (575 mL) and purged with argon. Pd(OH)$_2$/C (25 g, 20 wt %) was added and a stream of H$_2$ gas was bubbled through the solution via a balloon and a long syringe needle. The reaction was stirred vigorously for 6 hours, replenishing the H$_2$ balloon as necessary (3×). The reaction was monitored by TLC (20% MeOH in DCM) and LCMS. Upon completion the reaction mixture was filtered thru a pad of celite. The filtrate was concentrated under reduced pressure to provide a tan syrup that was dissolved in DCM (500 mL) and transferred to a separatory funnel. The reaction mixture was washed with 1:1 H$_2$O and brine (1×500 mL), then NaHSO$_4$ (0.2M, 2×500 mL), followed by H$_2$O (1×500 mL), and finally washed with brine (1×500 mL). The organics were collected, dried over MgSO$_4$, filtered and concentrated to provide the crude material as a sticky foam. The crude Compound 13b was used without further purification in the next step.

Crude Compound 13b was (138 g, 52.9 mmol theoretical) was dissolved in dry DCM (525 mL) and diisopropylethylamine (DIEA) was added (37 mL, 4 eq.). The reaction was purged with nitrogen and PFP-TFA was added slowly to the reaction mixture via syringe (18 mL, 105 mmol, 2 eq.). The color of the reaction changed from pale yellow to pale orange, and gave off a light smoke which was blown away with a stream of nitrogen. Additional DIEA was added to bring the reaction to pH=9-10 (53 mL DIEA total). The reaction was allowed to stir at room temperature for one hour, during which time the reaction turned magenta in color. Completion of reaction was confirmed by LCMS. The reaction was washed with NaHSO$_4$ (0.2M, 1×500 mL) followed by water (1×500 mL). The reaction mixture was washed with 1:1 H$_2$O and saturated aqueous NaHCO$_3$ until the level of PFP—OH was less than 10% (4×400 mL). The organic layer was collected, washed with brine (1×500 mL), dried over MgSO$_4$, filtered and concentrated to a sticky foam which was dissolved in EtOAc (150 mL). The reaction was stirred vigorously, and hexanes (500 mL) was added. A sticky white solid formed, and deposited as a gum on the walls of the flask. The reaction was allowed to sit for 20 minutes, then the solvent was decanted. The precipitation process was repeated. The resulting combined gum was dried under high vacuum to give Compound 13c (95 g, 95% from Compound 7) as a brittle white foam. The structure of Compound 13c was confirmed by LCMS, $^1$H NMR and $^{19}$F NMR.

Alternate Method for the Preparation of Compound 13b

To a 1 L pressure bottle (parr hydrogenator) was added THF (110 mL) followed by Compound 11 (25.5 g, 0.044 mol, 3.05 eq.) under nitrogen. The bottle was agitated manually for 10 minutes. To the bottle was added Compound 7 (15.0 g, 0.014 mol, 1 eq.), with the transfer completed using THF (20 mL). The bottle was purged with nitrogen and the mixture was stirred/agitated for about 15 minutes. Palladium hydroxide (Pd(OH)$_2$, 4.2 g) was added under nitrogen and the bottle was attached to the hydrogenator. The bottle was flushed with nitrogen (2×15 psi) followed by a hydrogen flush (2×15 psi). The bottle was pressurized with hydrogen (15-20 PSI) and agitated with continuous monitoring to record hydrogen uptake.

| Reaction time (min.) | H$_2$ pressure (psi) | Action |
|---|---|---|
| 0 | 20 | start |
| 10 | 10 | |
| 15 | 8 | |
| 16 | 22 | repressurize to 22 psi |
| 30 | 20 | |
| 45 | 18 | |
| 60 | 18 | |
| 70 | 18 | Completion. |

At 70 minutes the reaction was worked up as no tris-PFP ester, Compound 7 was remaining by TLC. The mixture was filtered under an atmosphere of nitrogen through about a 1.5 inch tall celite bed (pre-washed with THF). The filter cake was washed THF (2×20 mL). The combined filtrate was then concentrated with warming from 30-40° C. under high vacuum to give crude Compound 13b as a semi-solid foam. The crude material was purified by silica gel column chromatography as illustrated above to provide Compound 13b (18.4 g, 81%) as a light yellow foam. The structure of Compound 13b was confirmed by LCMS and $^1$H NMR.

Example 8

Preparation of Compound 13c

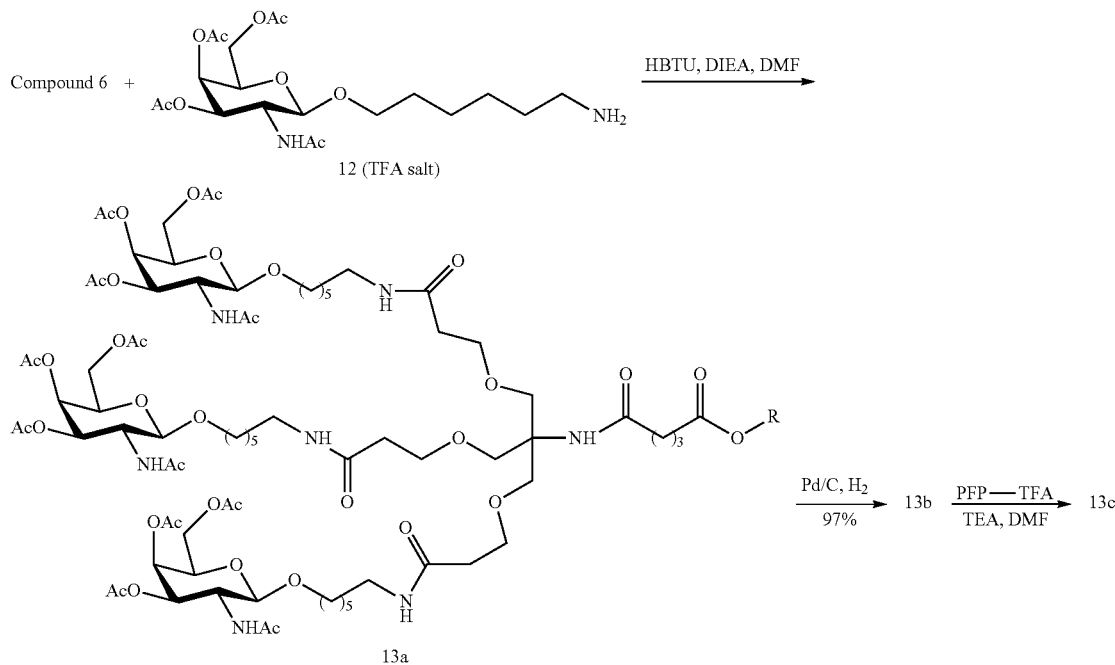

Compound 13a: R = Bn
Compound 13b: R = H
Compound 13c: R = pentafluorophenyl

Compound 6 (4.0 g), HBTU (9.8 g) and DIEA were dissolved in DMF (30 mL) and stirred at room temperature for 5 minutes. A solution of Compound 12 in DMF (12.4 g in 30 mL) was added. The reaction was stirred at room temperature and monitored by LCMS. The reaction was complete after 2 hours of stirring. The reaction mixture was concentrated under reduced pressure at 50° C. The residue was diluted with dichloromethane and resulting organic phase was washed with water, 1N NaHSO$_4$, brine, filtered and dried over anhydrous Na$_2$SO$_4$. The organic phase was concentrated to dryness and the residue was purified by silica gel column chromatography and eluted with ethyl acetate (2 CV), 2% MeOH in ethyl acetate (2 CV), 5% MeOH in ethyl acetate (4 CV), 8% MeOH in ethyl acetate (4 CV), 10% MeOH in ethyl acetate (4 CV) and 15% MeOH in ethyl acetate (8 CV). Compound 13a (11.26 g, 83%) was eluted at 10-15% methanol in dichloromethane. The structure of Compound 13a was confirmed by LCMS and $^1$H NMR.

Compound 13a (9.9 g) and Pd/C (1 g) were suspended in a mixture of methanol (20 mL) and ethyl acetate (20 mL) and hydrogenated under hydrogen atmosphere pressure (balloon). The reaction was complete after 12 hours as monitored by LC MS. The catalyst was filtered through a celite pad and celite pad was washed thoroughly using methanol/ethyl acetate mixture (200 mL, 1:1). The combined organic solutions were concentrated to dryness to provide compound 13b (9.32 g) as a white foam. The structure of Compound 13b was confirmed by LCMS and $^1$H NMR.

Compound 13b (9.15 g) and TEA (2.2 mL, 3 eq.) were dissolved in DMF (40 mL) and PFP-TFA (1.81 mL, 2 eq.) was added (color changed from yellow to burgundy). After one hour, LCMS showed that the reaction was completed. The DMF was removed under reduced pressure at 70° C. 1N NaHSO$_4$ (100 mL) was added and the mixture was extracted with dichloromethane, washed with brine, saturated sodium bicarbonate, brine, dried over Na$_2$SO$_4$ and concentrated to dryness. Compound 13c (9.67 g) was obtained as yellow foam. The structure of Compound 13c was confirmed by LCMS, $^1$H NMR and $^{19}$F NMR.

Example 9

Preparation of Compound 18

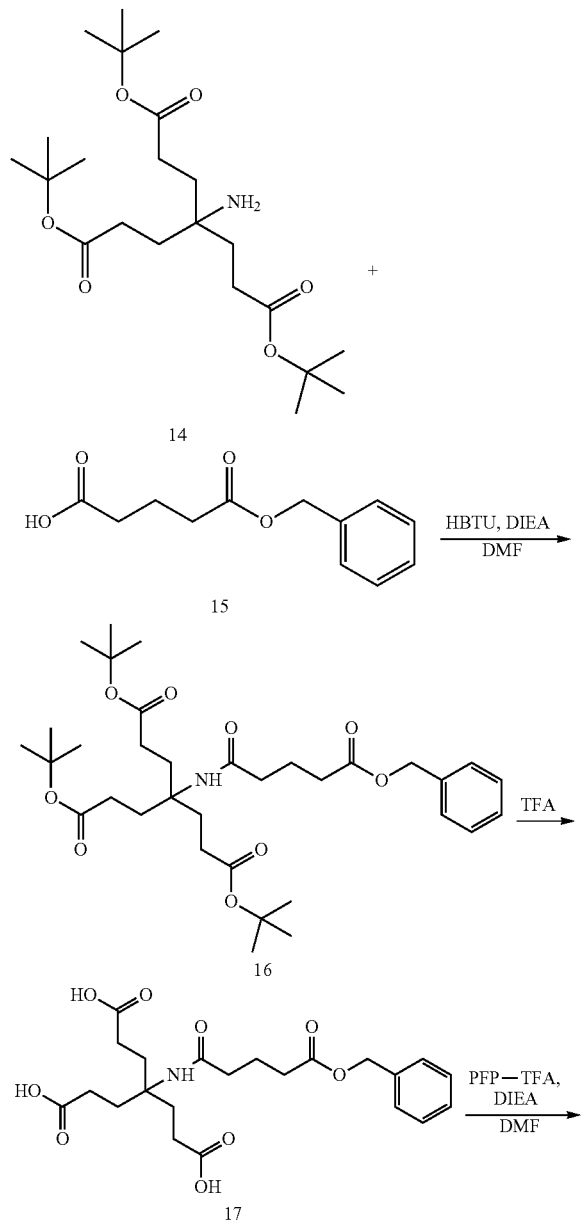

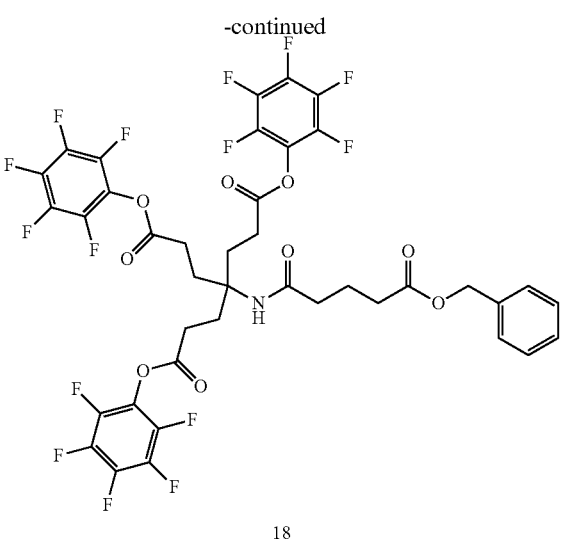

Compound 15 (6.95 g, 31.28 mmol, commercially available) was treated with HBTU (11.86 g, 31.28 mmol) and DIEA (8.24 ml, 48.13 mmol) in DMF (60 mL) for 15 minutes at room temperature. This solution was then added to a solution of Compound 14 (10 g, 24.06 mmol, commercially available) in 60 mL of DMF. After stirring at room temperature for 16 hours, complete conversion to Compound 16 was observed by LCMS. The reaction was poured onto 400 mL EtOAc and 500 mL water. The organic layer was separated and washed with additional water, brine and then dried over Na$_2$SO$_4$. The organic layer was then filtered and evaporated under reduced pressure to yield 17.05 g of Compound 16 as a brown oil. The oil was then treated with TFA (50 mL) and DCM (150 mL) for 8 hours, and complete conversion to Compound 17 was observed by LCMS. Solvent was evaporated and co-evaporated with toluene at 50-60° C. under reduced pressure to yield a brown oil.

After drying for 16 hours under high vacuum, this oil was dissolved in DMF (200 mL). DIEA (19.88 ml, 116.15 mmol) was added and the solution was stirred under an inert atmosphere in an ice bath. Pentafluorophenyl trifluoroacetate (10.98 ml, 63.88 mmol) was then added dropwise, and the reaction was allowed to proceed at room temperature for an hour, at which time complete conversion to Compound 18 was observed by LCMS. The reaction was poured onto ice, extracted with EtOAC, and the organic layer washed successively with water, brine and then dried over Na$_2$SO$_4$. The organic layer was then filtered and evaporated under reduced pressure to yield 25.5 g of a brown/tan sticky solid. The solid was dissolved in a mixture of EtOAc (20 mL) and heptane (220 mL) at 70 C, and then allowed to cool to room temperature with stirring. The resultant solid was collected by filtration, washed with hexanes, and dried under reduced pressure to yield Compound 18 (13.36 g, 58% over three steps) as a white/tan solid. LCMS, $^1$H NMR and $^{19}$F NMR were consistent with the structure.

Example 10

Preparation of Compound 19

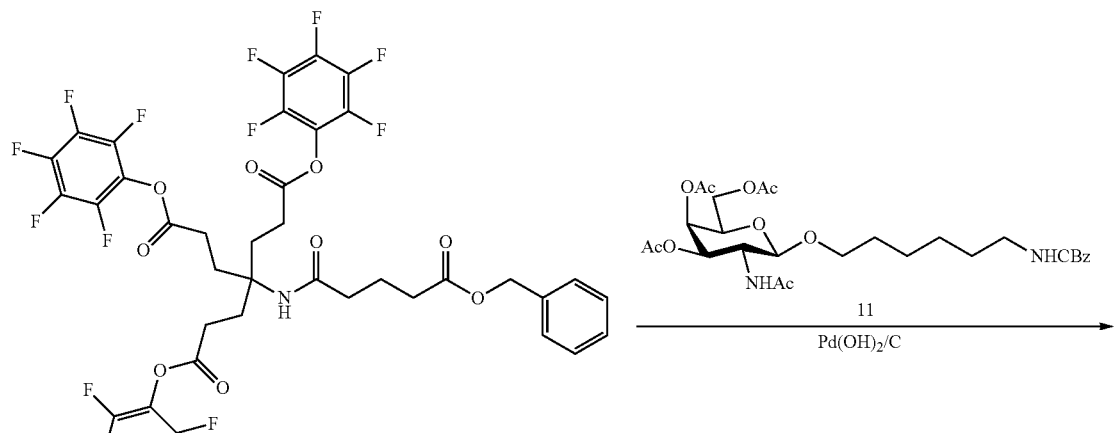

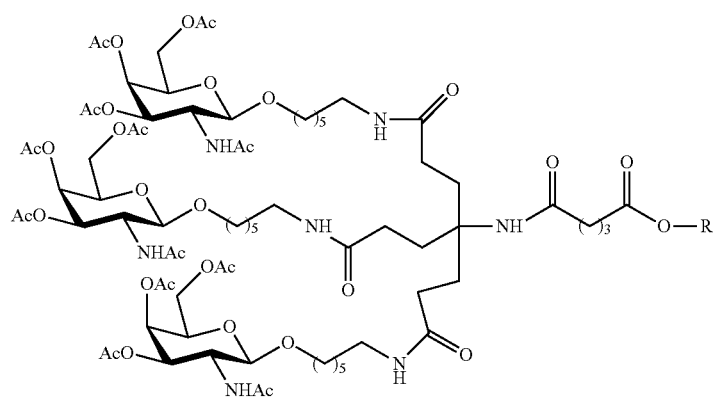

Compound 19b: R = H
Compound 19c: R = pentafluorophenyl

A solution of Compound 11 (21 g, 36.17 mmol), Compound 18 (10.61 g, 11.17 mmol) and Pd(OH)$_2$/C (20 wt %, 1.3 g, 1.9 mmol) was stirred in acetonitrile (120 mL) at 1 atm for 5 hours. At that time, the reaction was filtered thru Celite and evaporated to a brown foam. To this foam was added 175 mL of EtOAc to give a brown solution. 175 mL of heptane was added with stirring to give a very sticky white solid. The EtOAc/heptane was decanted and 175 mL of hexanes was added, which was also decanted. The white sticky solid was then dried under reduced pressure for 24 hours to give 21.7 g of Compound 19b. LCMS and $^1$H NMR were consistent with structure.

Compound 19b (5.2 g) and TEA (1.14 mL, 3 eq.) were dissolved in DMF (25 mL). To this PFP-TFA (0.937 mL, 2 eq.) was added (color changed from yellow to burgundy) dropwise. The reaction was completed after one hour as determined by LC MS analysis. The DMF was removed under reduced pressure at 50° C. The residue was diluted with dichloromethane and the organic phase was washed with 1N NaHSO$_4$ (80 mL), saturated aqueous sodium bicarbonate solution and brine. The organic phase was dried over Na$_2$SO$_4$, filtered and evaporated to yield 19c (5.71 g, quantitative) as a light pink foam. The structure of Compound 19c was confirmed by LCMS, $^1$H NMR and $^{19}$F NMR.

Example 11

Preparation of Compound 22

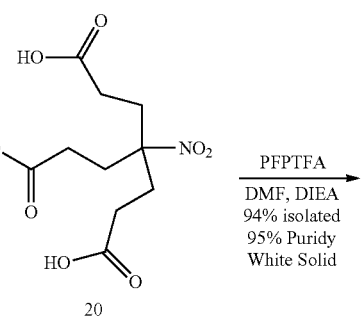

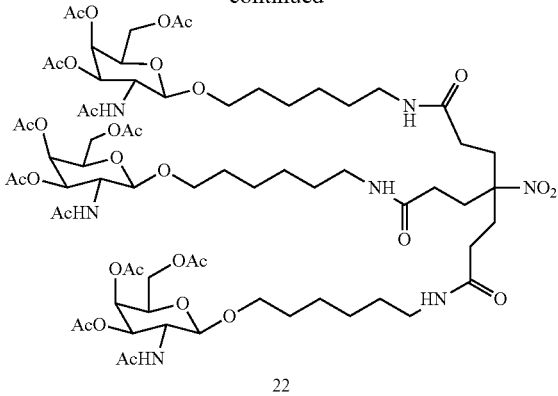

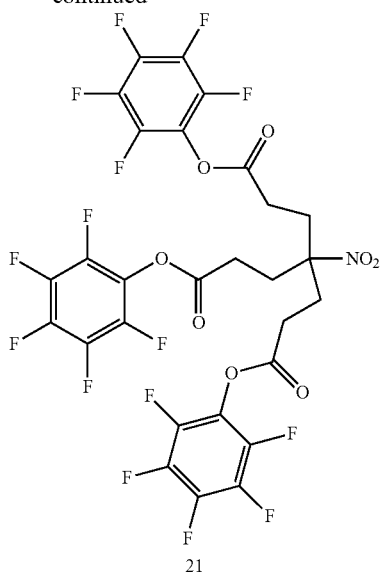

Triacid 20 (4 g, 14.43 mmol) was dissolved in DMF (120 mL) and diisopropylethylamine (12.35 mL, 72 mmoles). Pentaflourotriflouroacetate (PFPTFA, 8.9 mL, 52 mmoles) was added dropwise, under argon, and the reaction was allowed to stir at room temperature for 30 minutes. The reaction mixture was poured onto water, extracted with ethyl acetate, and the organic layer was washed successively with water and brine. The organic layer was dried over sodium sulfate, and evaporated to provide Compound 21 as a white solid. The yield was 94% and the NMR and LCMS data were consistent with structure.

Compound 21 (12.5 g, 16.12 mmole), compound 11 (28.9 g, 49.86 mmole) and 20% Pd/C (1 g) in EtOAc/MeOH (3:1, 200 mL) was hydrogenated at room temperature and 1 atmosphere for 3.5 hours. The reaction mixture was filtered thru a bed of celite and evaporated to dryness. The crude Compound 22 was purified by silica gel chromatography (eluting with 5 to 10% methanol/dichloromethane) to provide 25.2 g of Compound 22 (85.5%). The NMR and LCMS spectra were consistent with the structure.

Example 12

Preparation of Compound 27

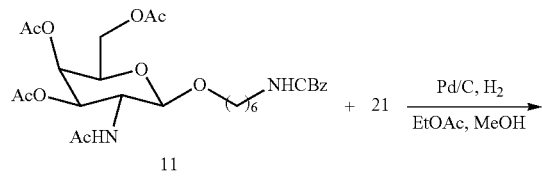

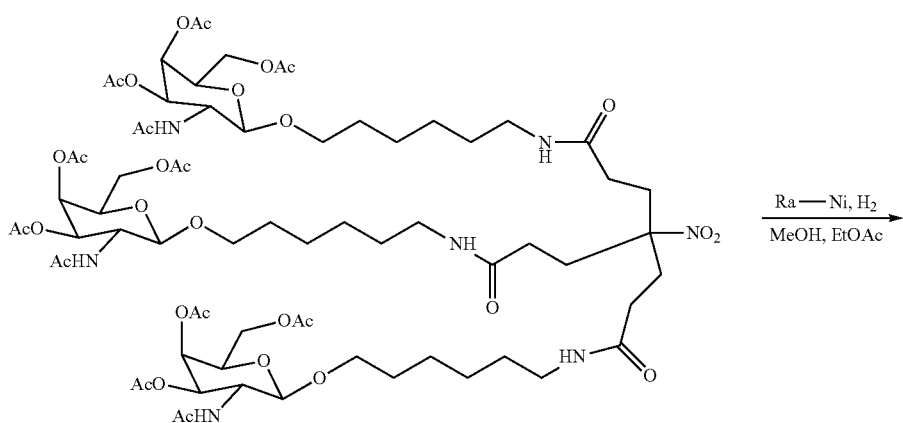

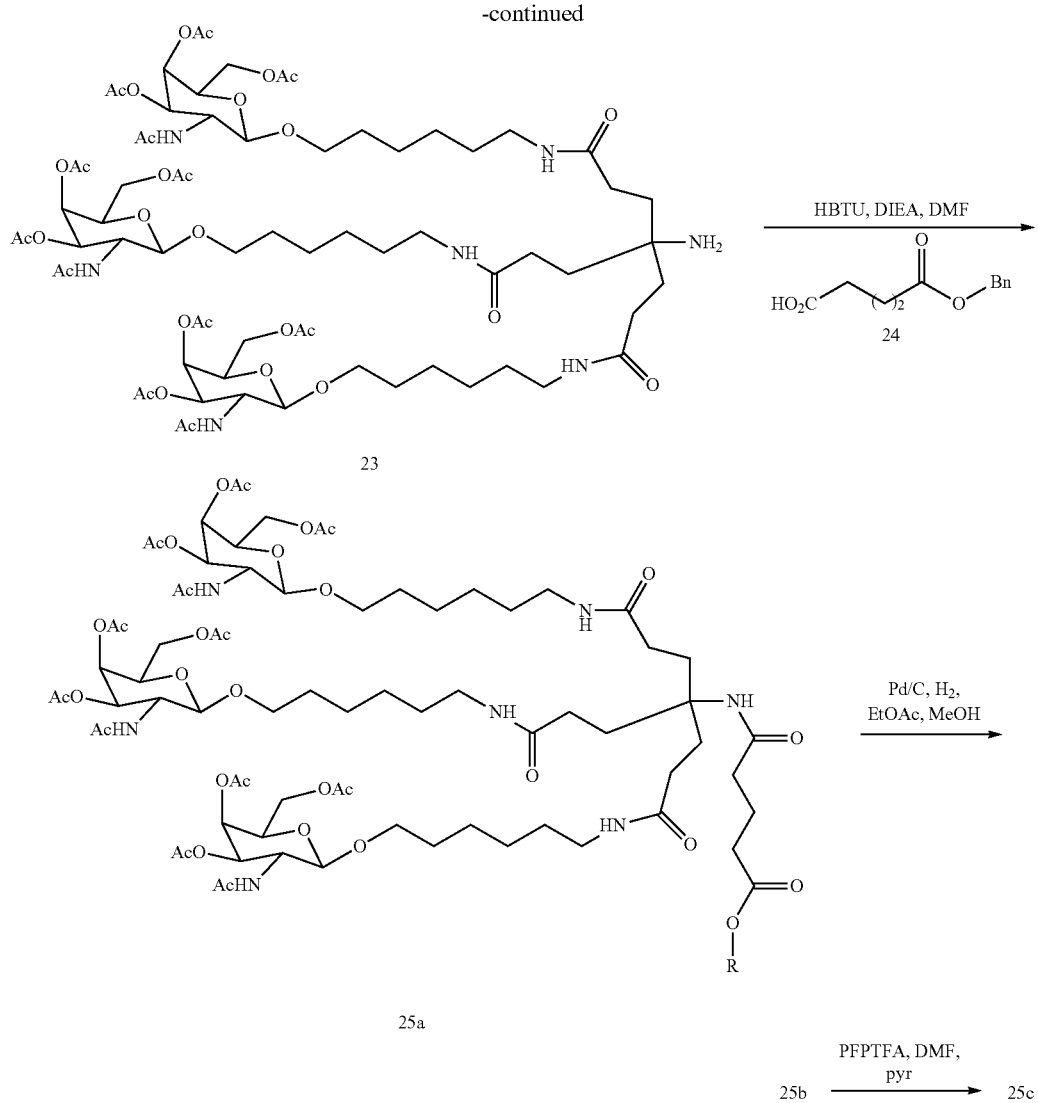

Compound 25a: R = Bn
Compound 25b: R = H
Compound 25c: R = pentafluorophenyl

Compound 22 (0.75 mmoles) was hydrogenated over Raney Nickel for 3 hours in Ethanol (75 mL). The catalyst was removed by filtration thru celite, and the ethanol removed under reduced pressure to give Compound 23 in 80-90% yield. LCMS and proton NMR were consistent with the structure.

Compound 24 (0.17 g, 0.76 mmoles) was treated with HBTU (0.29 g, 0.76 mmoles) and N,N-diisopropylethylamine (0.35 mL, 2.0 mmoles) in DMF (50 mL) for 15 minutes. To this was added compound 23 (0.51 mmoles) with stirring at room temperature for 16 hours. The DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5% to 20% methanol/dichloromethane) to provide Compound 25a in 40-60% yield. LCMS and proton NMR was consistent with the structure.

Compound 25a (0.16 mmoles), was hydrogenated over 10% Pd(OH)$_2$/C for 3 hours in methanol/ethyl acetate (1:1, 50 mL). The catalyst was removed by filtration thru celite, and the organics removed under reduced pressure to give Compound 25b in 80-90% yield. LCMS and proton NMR was consistent with the structure.

Compound 25b (0.15 mmoles), was dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. The DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→5% methanol/dichloromethane) to provide Compound 25c in an approximate 80% yield. LCMS and proton NMR were consistent with the structure.

Example 13

General Method for Conjugation of GalNAc₃ Cluster to an Oligomeric Compound (OLIGO)

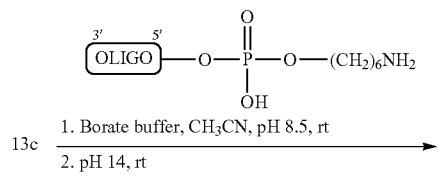

1. Borate buffer, CH₃CN, pH 8.5, rt
2. pH 14, rt

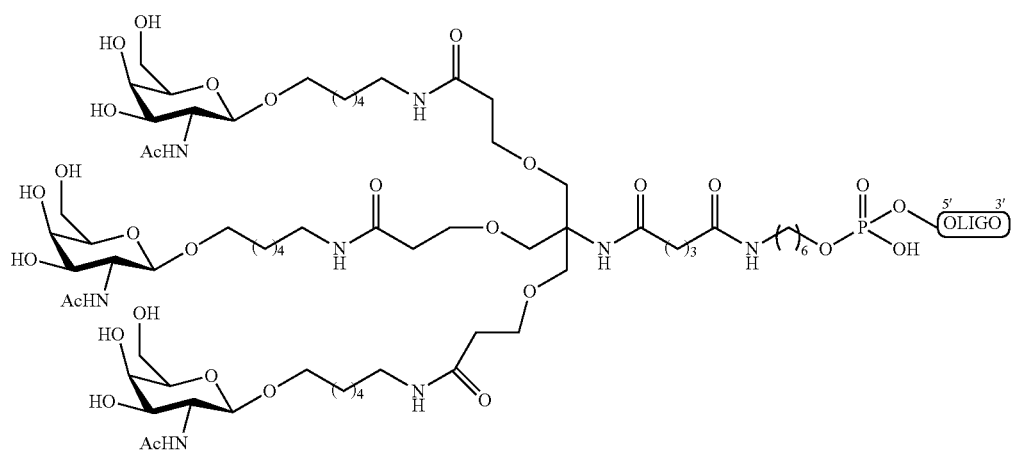

26

A 5'-hexylamino modified oligonucleotide was synthesized and purified using standard solid-phase oligonucleotide procedures. The 5'-hexylamino modified oligomeric compound (1.33 mmol) was dissolved in 0.1 M sodium tetraborate, pH 8.5 (180 mL) and 2-3 equivalents of a selected PFP esterified GalNAc₃ cluster (13c exemplified, see also 19c and 25c) dissolved in acetonitrile or an acetonitrile/DMSO mixture (50-65 mL) was added. The reaction was complete after about 3-6 h of mixing at room temperature. The pH of the resulting solution was adjusted to 14-16 using 1N NaOH solution and stirring continued for 4-6 h. The conjugated oligomeric compound was purified and desalted by RP-HPLC and lyophilized to provide the GalNAc₃ conjugated oligomeric compound.

Example 14

Method for Conjugation of GalNAc₃ Cluster to an Oligomeric Compound (OLIGO) Alternate Method

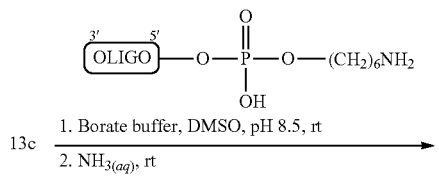

1. Borate buffer, DMSO, pH 8.5, rt
2. NH₃(aq), rt

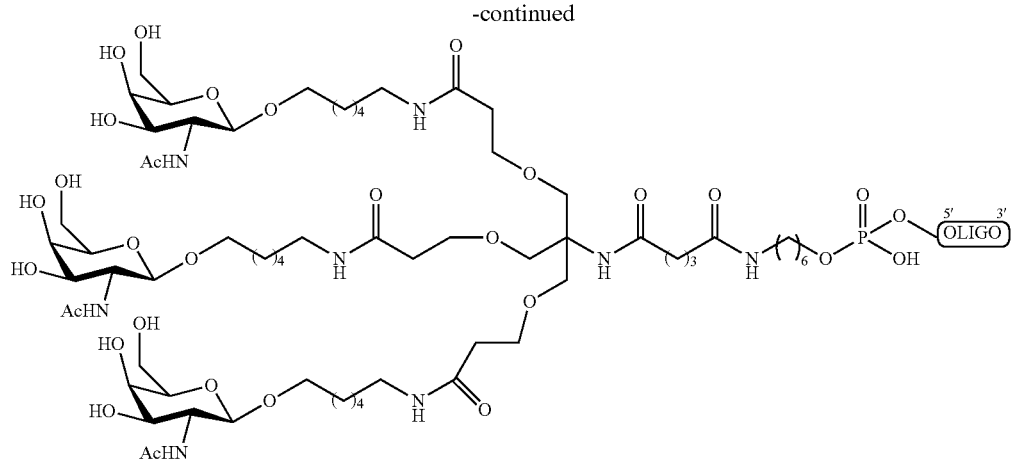

26

A 5'-hexylamino modified oligomeric compound was synthesized and purified using standard solid-phase oligonucleotide procedures. The 5'-hexylamino modified oligomeric compound (1.33 mmol) was dissolved in 0.1 M sodium tetraborate, pH 8.5 (180 mL) and 2-3 equivalents of a selected PFP esterified GalNAc$_3$ cluster (13c exemplified, see also 19c and 25c) dissolved in DMSO, acetonitrile, or an acetonitrile/DMSO mixture (50-65 mL) was added. The reaction was complete after about 16 h of mixing at room temperature. The resulting solution was diluted with water, then spun at 3000 rpm in a slin filter with a mass cut-off of 3 kDa. This process was repeated twice to remove small molecule impurities. The solution was then lyophilized to dryness and redissolved in concentrated aqueous ammonia and mixed at room temperature for 2.5 h followed by concentration in vacuo to remove most of the ammonia. The conjugated oligomeric compound was purified and desalted by RP-HPLC and lyophilized to provide the GalNAc$_3$ conjugated oligomeric compound.

Example 15

General Method for Conjugation of GalNAc$_3$ Cluster to a Nucleoside or Other Small Molecule

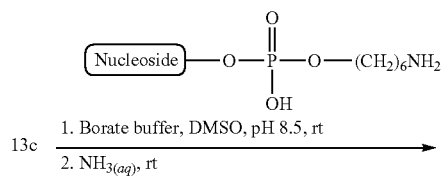

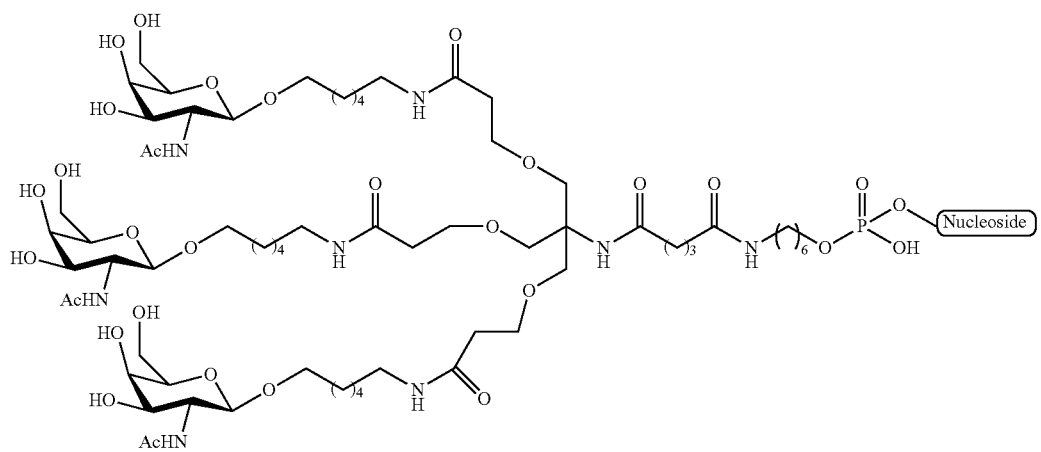

27

A hexylamino containing nucleoside phosphate is prepared by standard methods and conjugated to a GalNAc$_3$ cluster (13c exemplified, see also 19c and 25c) according to the procedure described in Example 12 or Example 11 above. Similar methods can be used to conjugate a GalNAc$_3$ cluster to an amine containing small molecule or small molecule that has been modified to contain an amine.

Example 16

General Method for Conjugation of a GalNAc$_3$ Cluster to a Peptide

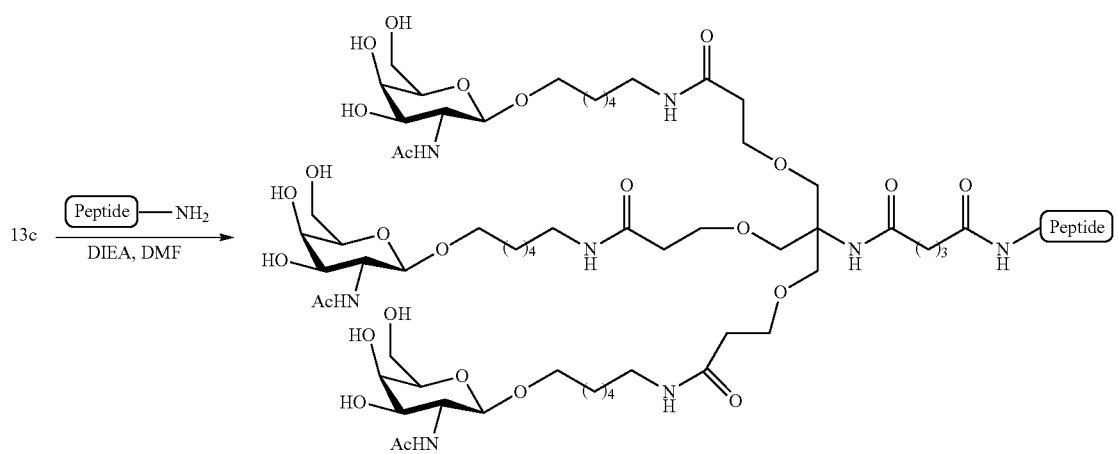

A peptide is prepared according to standard peptide synthesis methods. The N-terminal amine or a side chain amine is conjugated to a GalNAc$_3$ cluster (13c exemplified, see also 19c and 25c) using DIEA in DMF.

Example 17

General Method for Conjugation of a GalNAc$_3$ Cluster to a Protein

A protein is prepared via standard recombinant and/or synthetic methods. The reaction with an activated GalNAc$_3$ cluster (13c exemplified, see also 19c and 25c) takes place in buffer or a mixture of buffer and DMSO used to dissolve the starting materials.

What is claimed is:

1. A method for synthesis of a reactive conjugate cluster having the formula:

$$(L\text{-}A\text{-}N(H)C(\!\!=\!\!O)\text{-}E\text{-})_m\text{-}Bg_a$$

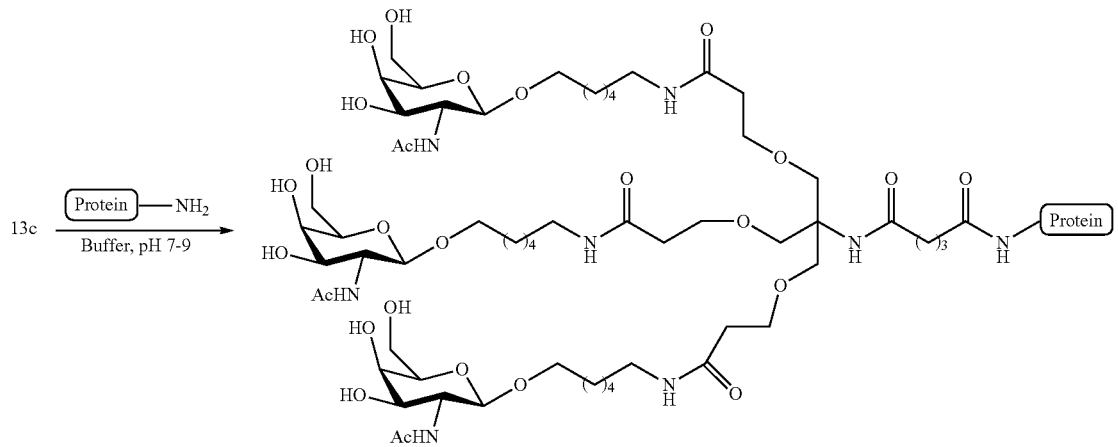

wherein:
  L is a ligand;
  A is $C_2$ to $C_{10}$ alkyl optionally interrupted with one or more groups selected from —O—, —N(H)— and C(=O);
  E is a single bond or $C_1$ to $C_{10}$ alkyl optionally interrupted with one or more groups selected from —O—, —N(H)— and C(=O);
  $Bg_a$ is a reactive branching group;
  m is from 2 to about 6;

comprising:
reacting a pentafluorophenyl ester protected branching group having the formula:

(PFP—O—C(=O)-E-)$_m$-Bg$_a$;

with at least m equivalents of a functionalized ligand having the formula:

L-A-N(H)Pg$_2$ wherein Pg$_2$ is an amino protecting group;
in an organic solvent with a palladium catalyst and H$_2$ for a time and under conditions sufficient to provide the reactive conjugate cluster.

2. The method of claim 1 wherein each E is C$_1$ to C$_4$ alkyl.
3. The method of claim 1 wherein each E is CH$_2$.
4. The method of claim 1 wherein each E is a single bond.
5. The method of claim 1 wherein the reactive branching group has the formula:

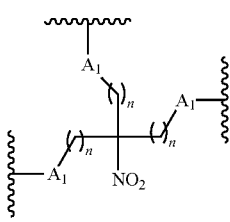

wherein:
each A$_1$ is, independently, CH$_2$, O or N(H); and
each n is, independently, 1 or 2.

6. The method claim 1, wherein the reactive branching group has the formula:

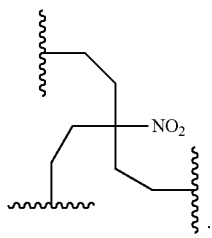 [SMILES: *CCC(CC*)(CC*)[N+](=O)[O-]]

7. The method of claim 1, wherein the reactive branching group has the formula:

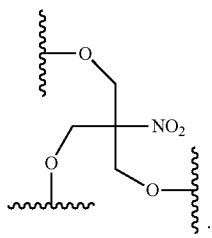 [SMILES: *OCC(CO*)(CO*)[N+](=O)[O-]]

8. The method of claim 1, wherein m is 3.
9. The method of claim 1 wherein the pentafluorophenyl ester protected branching group has the formula:

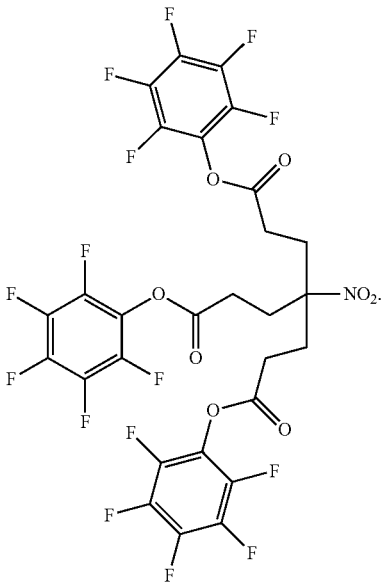 [SMILES: O=C(CCC(CCC(=O)Oc1c(F)c(F)c(F)c(F)c1F)(CCC(=O)Oc1c(F)c(F)c(F)c(F)c1F)[N+](=O)[O-])Oc1c(F)c(F)c(F)c(F)c1F]

10. The method of claim 1, wherein the pentafluorophenyl ester protected branching group is at least 95% pure.
11. The method of claim 1, wherein each L has the formula:

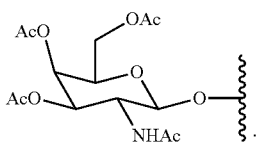 [SMILES: *OC1OC(COC(C)=O)C(OC(C)=O)C(OC(C)=O)C1NC(C)=O]

12. The method of claim 1, wherein the functionalized ligand has the formula:

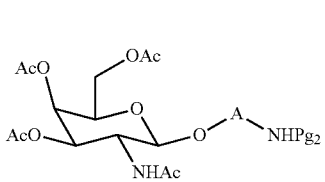

wherein
A is C$_2$ to C$_{10}$ alkyl optionally interrupted with one or more groups selected from —O—, —N(H)— and C(=O);
Pg$_2$ is an amino protecting group.
13. The method of claim 1, wherein the functionalized ligand is prepared by treating a first intermediate having the formula:

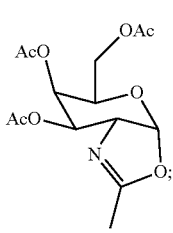

with a second intermediate having the formula:

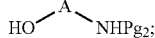

for a time and under conditions to provide the functionalized ligand; and wherein the first intermediate is prepared in situ by treatment of the protected galactose sugar having the formula:

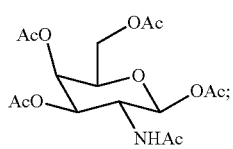 [SMILES: CC(=O)NC1C(OC(C)=O)OC(COC(C)=O)C(OC(C)=O)C1OC(C)=O]

in an organic solvent with trimethylsilyl triflate (TMSOTf).

14. The method of claim 1, wherein each A is $C_4$ to $C_8$ alkyl.

15. The method of claim 1, wherein each A is $C_4$ to $C_8$ alkyl interrupted with one amide group (—N(H)—C(=O)—).

16. The method of claim 13, wherein the second intermediate has the formula:

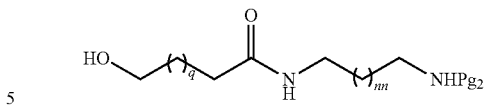

wherein q is from 1 to 4; and
nn is from 1 to 6.

17. The method of claim 13, wherein the second intermediate is prepared by treating a cyclic compound having the formula:

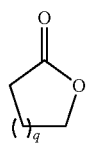

wherein q is from 1 to 4;
with a diamine compound having the formula:

;
isolating the crude product; and
treating the crude product with a reagent to protect the free amino group to provide the second intermediate.

18. The method of claim 17 wherein q is 2.
19. The method of claim 17 wherein q is 3.
20. The method of claim 17 wherein nn is 1.

* * * * *